United States Patent
Welsh et al.

(10) Patent No.: US 6,649,597 B1
(45) Date of Patent: Nov. 18, 2003

(54) TARGETING VECTOR TO THE UROKINASE PLASMINOGEN ACTIVATOR RECEPTOR

(75) Inventors: Michael J. Welsh, Riverside, IA (US); Paola T. Drapkin, Iowa City, IA (US)

(73) Assignee: The University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/599,846

(22) Filed: Jun. 22, 2000

(51) Int. Cl.$^7$ .......................... A61K 31/70; A61K 38/00; C12N 15/74; C12P 21/06

(52) U.S. Cl. .......................... 514/44; 514/2; 435/320.1; 435/69.1

(58) Field of Search .............................. 435/320.1, 69.1; 514/44, 2

(56) References Cited

U.S. PATENT DOCUMENTS

| | | | |
|---|---|---|---|
| 5,550,213 A | 8/1996 | Anderson et al. ............ 530/326 |
| 5,656,269 A | 8/1997 | Haigwood et al. ........ 424/94.63 |
| 5,656,726 A | 8/1997 | Rosenberg et al. .......... 530/326 |
| 5,679,350 A | 10/1997 | Jakun et al. ................. 530/326 |
| 5,679,782 A | 10/1997 | Rosenberg et al. ......... 576/23.1 |
| 5,759,542 A | 6/1998 | Gurewich ................ 424/94.64 |
| 5,882,877 A | 3/1999 | Gregory et al. ........... 435/320.1 |
| 5,891,664 A | 4/1999 | Danø et al. ................. 435/69.1 |
| 5,942,492 A | 8/1999 | Jones et al. .................... 514/15 |
| 6,287,857 B1 * | 9/2001 | O'Riordan et al. |

FOREIGN PATENT DOCUMENTS

| WO | WO 9012091 | 10/1990 |
|---|---|---|
| WO | WO 9705257 | 2/1997 |
| WO | WO 9846632 | 10/1998 |
| WO | WO 9846731 | 10/1998 |
| WO | WO 9846781 | 10/1998 |

OTHER PUBLICATIONS

N Hattori et al., Lung Cell. Mol. Physiol., "Participation of urokinase–type plasminogen activator receptor in the clearance of fibrin from the lung," 1991, 21, pp. L573–L579.*

N Hattori et al., Human Gene Therapy, "Upregulation of Fibrinolysis by Adenovirus–Mediated Transfer of Urokinase–Type Plasminogen Activator Genes to Lung Cells in Vitro and in Vivo," Jan. 1999, 10:215–222.*

TA Kost et al., Elsevier Science, "Production of a urokinase plasminogen activator–IgG fusion protein(uPA–IgG) in the baculovirus expression system" Apr. 1997, 190:139–144.*

RC Boucher, Journal of Clin. Investigation, "Status of gene therapy for cystic fibrosis lung disease," Feb. 1999, vol. 103, No. 4, pp. 441–445.*

SL Eck et al., Gene–Based Therapy, "Scope of Gene Therapy," 1995, 9th Ed., Chap.5, pp. 77–101.*

Drapkin et al., 2000, "Targeting the urokinase plasminogen activator receptor enhances gene transfer to human airway epithelia", *Journal of Clnical Investigation* 105:589–596.

Walters et al., 2000, "Incorporation of Adeno–Associated Virus in a Calcium Phosphate Coprecipitate Improves Gene Transfer to Airway Epithelia In Vitro and In Vivo", *J. Virol.* 74:535–540.

Chiorini et al., 1999, "Cloning and Characterization of Adeno–Associated Virus Type 5", *J. Virol.* 73:1309–1319.

Drapkin et al., Oct. 7–10, 1999, "Targeting Adenovirus Binding to the Apical Membrane of human Airway Epithelia", Thirteenth Annual North American Cystic Fibrosis Conference, Seattle, WA, *Pediatric Pulmonol.* Suppl. 19:224 (Abstract 211).

Drapkin et al., Jun. 9–13, 1999, "Targeting adenovirus binding to the apical membrane of human airway epithelia", American Society of Gene Therapy, 2nd Annual Meeting, Washington, D.C., Abstract 753.

Lee et al., 1999, "Delivery of an Adenovirus Vector in a Calcium Phosphate Coprecipitate Enhances the Therapeutic Index of Gene Transfer to Airway Epithelia", *Hum. Gene Ther.* 10:603–613.

O'Riordan et al., 1999, "PEGylation of Adenovirus with Retention of Infectivity and Protection from Neutralizing Antibody in Vitro and in Vivo", *Human Gene Ther.* 10:1349–1358.

Vilhardt et al., 1999, "Urokinase–Type Plasminogen Activator Receptor Is Internalized by Different Mechanisms in Polarized and Nonpolarized Madin–Darby Canine Kidney Epithelial Cells", *Mol. Biol. Cell* 10:179–195.

Walters et al., 1999, "Basolateral Localization of Fiber Receptors Limits Adenovirus Infection from the Apical Surface of Airway Epithelia", *J. Biol. Chem.* 274:10219–10226.

Wei et al., 1999, "A Role for Caveolin and the Urokinase Receptor in Integrin–mediated Adhesion and Signaling", *J. Cell Biol.* 144:1285–1292.

(List continued on next page.)

*Primary Examiner*—Anne M. Wehbe
*Assistant Examiner*—Janice Li
(74) *Attorney, Agent, or Firm*—Baker Botts L.L.P.

(57) ABSTRACT

The present invention relates to the targeted delivery of a delivery vehicle construct which specifically binds to and stimulates endocytosis into cells expressing the urokinase plasminogen activator receptor (uPAR), and particularly human airway epithelia. The delivery vehicle construct comprises a portion of uPA and a cargo linked thereto and is useful for the targeted delivery of the cargo to a cell. In one aspect of the invention, the uPA portion of the delivery vehicle construct comprises the wild-type uPA, a fragment of uPA which has the PAI-1 binding region deleted, or a uPA peptide comprising amino acids 13–19 and is useful for the targeted delivery of the cargo to cells, and in particular to airway epithelia. The present invention also provides a method for delivering the delivery vehicle construct to a cell. The method comprises the steps of (a) contacting a target cell with a delivery vehicle construct comprising a uPA portion and a cargo portion; and (b) obtaining a desired result in the target cell.

10 Claims, 7 Drawing Sheets

OTHER PUBLICATIONS

Duan et al., 1998, "Polarity Influences the Efficiency of Recombinant Adenoassociated Virus Infection in Differentiated Airway Epithelia", *Hum. Gene Ther.* 9:2761–2776.

Fasbender et al., 1998, "Incorporation of Adenovirus in Calcium Phosphate Precipitates Enhances Gene Transfer to Airway Epithelia In Vitro and In Vivo", *J. Clin. Invest.* 102:184–193.

Middleton et al., 1998, "Gene Therapy for Cystic Fibrosis: Which Postman, Which Box?", *Thorax* 53:197–199.

Pickles et al., 1998, "Limited Entry of Adenovirus Vectors into Well–Differentiated Airway Epithelium is Responsible for Inefficient Gene Transfer", *J. Virol.* 72:6014–6023.

Quax et al., 1998, "Binding of Human Urokinae–Type Plasminogen Activator to Its Receptor", *Arterioscler. Thromb. Vasc. Biol.* 18:693–701.

Rodenberg et al., 1998, "Binding of Urokinase–Type Plasminogen Activator–plasminogen Activator Inhibitor–1 Complex to the Endocytosis Receptors $\alpha_2$–macroglobulin Receptor–low–density Lipoprotein Receptor–related Protein and Very–low–density Lipoprotein Receptor Involves Basic Residues in the Inhibitor", *Biochem J.* 329:55–63.

Summerford et al., 1998, "Membrane–Associated Heparan Sulfate Proteoglycan Is a Receptor for Adeno–Associated Virus Type 2 Virions", *J. Virol.* 72:1438–1445.

Teramato et al., 1998, "Factors Influencing Adeno–Associated Virus–Mediated Gene Transfer to Human Cystic Fibrosis Airway Epithelial Cells: Comparison with Adenovirus Vectors", *J. Virol.* 72:8904–8912.

Wang et al., 1998, "Influence of Cell Polarity on Retrovirus–Mediated Gene Transfer to Differentiated Human Airway Epithelia", *J. Virol.* 72:9818–9826.

Bergelson et al., 1997, "Isolation of a Common Receptor for Coxsackie B Viruses and Adenoviruses 2 and 5", *Science* 275:1320–1323.

Bürgle et al., 1997, "Inhibition of the interaction of urokinase–type plasminogen activator (uPA) with its receptor (uPAR) by synthetic peptides", *Biol. Chem.* 378:231–237.

Czekay et al., 1997, "Endocytic Trafficking of Megalin/RAP Complexes: Dissociation of the Comlexes in Late Endosomes", *Mol. Biol. Cell* 8:517–532.

Fasbender et al., 1997, "A low rate of cell proliferation and reduced DNA uptake limit cationic lipid–mediated gene transfer to primary cultures of ciliated human airway epithelia", *Gene Ther.* 4:1173–1180.

Goldman et al., 1997, "In Vitro and In Vivo Gene Delivery Mediated by a Synthetic Polycationic Amino Polymer", *Nat. Biotechnol.* 15:462–466.

Goretzki et al., 1997, "Receptor–mediated endocytosis of Urokinase–Type plasminogen activator is regulated by cAMP–dependent protein kinase", *J. Cell Sci.* 110:1395–1402.

Matsui et al., 1997, "Loss of Binding and Entry of Liposome–DNA Complexes Decreases Transfection Efficiency in Differentiated Airway Epithelial Cells", *J. Biol. Chem.* 272:1117–1126.

Robinson, 1997, "Signal transduction via GPI–anchored membrane proteins", in *ADP ribosylation in animal tissue.* Plenum Press, NY (1997) pp. 365–370.

Zhang et al., 1997, "Regulation of single chain urokinase binding, internalization, and degradation by a plasminogen activator inhibitor 1–derived peptide", *J. Biol. Chem.* 272:27053.

Kollen et al., 1996, "Gluconoylated and Glycosylated APolylysines As Vectors for Gene Transfer into Cystic Fibrosis Airway Epithelial Cells", *Hum. Gene. Ther.* 7:1577–1586.

Lu et al., 1996, "Blockage of Urokinase Receptor Reduces In Vitro the Motility and the Deformability of Endothelila Cells", *FEBS Lett.* 380:21–24.

Magdolen et al., 1996, "Systematic Mutational Analysis of the Receptor–Binding Region of the Human UrokinaseType Plasminogen Activator", *Eur. J. Biochem.* 237:743–751.

Zabner et al., 1996, "Adenovirus–Mediated Gene Transfer to Ciliated Airway Epithelia Requires Prolonged Incubation Time", *J. Virol.* 70:6994–7003.

Behrendt et al., 1995, "The Structure and Function of the Urokinase Receptor, a Membrane Protein Governing Plasminogen Activation on the Cell Surface", *Biol. Chem. Hoppe–Seyler* 376:269–279.

Conese et al., 1995, "Urokinase/Urokinase Receptor System: Internalization/Degradation of Urokinase–Serpin Complexes: Mechanism and Regulation", *Biol. Chem. Hoppe-Seyler* 376:143–155.

Crystal, 1995, "Transfer of Genes to Humans: Early Lessons and Obstacles to Success", *Science* 270:404–410.

Goldman et al., 1995, "Expression of $\alpha_v\beta_5$ Integrin Is Necessary for Efficient Adenovirus–Mediated Gene Transfer in the Human Airway", *J. Virol.* 69:5951–5958.

Heegaard et al., 1995, "Very Low Density Lipoprotein Receptor Binds and Mediates Endocytosis of Urokinase-Type Plasminogen Activator–Type–1 Plasminogen Activator Inhibitor Complex", *J. Biol. Chem.* 270:20855–20861.

Rao et al., 1995, "Urokinase Receptor Is a Multifunctional Protein: Influence of Receptor Occupancy on Macrophage Gene Expression", *J. Clin. Invest.* 96:465–474.

Schnaper et al., 1995, "Plasminogen Activators Augment Endothelial Cell Organization In Vitro by Two Distinct Pathways", *J. Cellul Physiol.* 164:107–118.

Wang et al., 1995, "Urokinase Receptor Mediates Mechanical Force Transfer Across the Cell Surface", *Am. J. Physiol.* 268:C1062–C1066.

Zabner et al., 1995, "Cellular and Molecular Barriers to Gene Transfer by a Cationic Lipid", *J. Biol. Chem.* 270:18997–19007.

Crystal et al., 1994, "Administration of an Adenovirus Containing the Human CFTR cDNA to the Respiratory Tract of Individuals with Cystic Fibrosis", *Nature Genetics* 8:42–51.

Dumler et al., 1994, "Interaction of Urokinase–Type plasminogenactivator (u–PA) with its cellular receptor (u–PAR) induces phosphorylation on tyrosine of a 38 kDa protein", *FEBS Lett.* 322:37–40.

Fazioli et al., 1994, "Urokinase–Type Plasminogen Activator and Its Receptor: New Targets for Anti–Metastatic Therapy?", *Trends Pharmacological Sci.* 15:25–29.

Jolly, 1994, "Viral Vector Systems for Gene Therapy", *Cancer Gene Therapy* 1:51–64.

Kobayashi et al., 1994, "Inhibition of Metastasis of Lewis Lung Carcinoma by a Synthetic Peptide within Growth Factor–Like Domain of Urokinase in the Experimental and Spontaneous Metastsis Model", *J. Cancer* 57:727–733.

Nykjaer et al., 1994, "Regions Involved in Binding of Urokinase–Type–1 Inhibitor Complex and Pro–Urokinase to the Endocytic $\alpha_2$–Macroglobulin Receptor/Low Density Lipoprotein Receptor–related Protein", *J. Biol. Chem.* 269:25668–25676.

O'Neal et al., 1994, "Somatic Gene Therapy for Cystic Fibrosis", *Hum. Mo. Genet.* 3:1497–1502.

Wei et al., 1994, "Identification of the Urokinase Receptor as an Adhesion Receptor for Vitronectin", *J. Biol. Chem.* 269:32380–32388.

Zabner et al., 1994, "Safety and Efficacy of Repetitive Adenovirus–mediated Transfer of CFTR cDNA to Airway Epithelia of Primates and Cotton Rats", *Nature Genetics* 6:75–83.

Moestrup et al., 1993, "Epithelial Glycoprotein–330 Mediates Endocytosis of Plaminogen Activator–Plasminogen Activator Inhibitor Type–1 Complexes", *J. Biol. Chem.* 268:16564–16570.

Rich et al., 1993, "Development and Analysis of Recombinant Adenoviruses for Gene Therapy of Cystic Fibrosis", *Human Gene Therapy* 4:461–476.

Zabner et al., 1993, "Adenovirus–mediated gene transfer transiently corrects the chloride transport defect in nasal epithelia of patients with cystic fibrosis", *Cell* 75:207–216.

Berkner, 1992, "Expression of Heterologous Sequences in Adenoviral Vectors", *Curr. Top. Micro. Immunol.* 158:39–66.

Martrisian, 1992, "The Matrix–Degrading Metalloproteinases", *Bioessays* 14:455–463.

Odekon et al., 1992, "Urokinases–Type Plasminogen Activator Mediates Basic Fibroblast Growth Factor–Induced Bovine Endothelial Cell Migration Independent of its Proteolytic Activity", *J. Cellul Physiol.* 150:258–263.

Rabbani et al., 1992, "Structural Requirements for the Growth Factor Activity of the Amino–terminal Domain of Urokinase", *J. Biol. Chem.* 267:14151–14156.

Yamaya et al., 1992, "Differential Stuctur and Function of Cultures from Human Trachela Epithelium", *Am. J. Physiol.* 262:L713–724.

Mignatti et al., 1991, "Expression of the Urokinase Receptor in Vascular Endothelial Cells Is Stimulated by Basic Fibroblast Growth Factor", *J. Cell Biol.* 113:1193–1201.

Robbiati et al., 1990, "A Recombinant Pro–urokinase Derived Mutant Missing the Growth Factor–like Domain Does Not Bind to its Receptor", *Fibrinolysis* 4:53–60.

Estreicher et al., 1989, "Characterization of the Cellular Binding Site for the Urokinase–type Plasminogen Activator", *J. Biol. Chem.* 264:1180–1189.

He et al., 1989, "Tissue Cooperation in a Proteolytic Cascade Activating Human Interstitial Collagenase", *Proc. Natl. Acad. Sci. USA* 86:2632–2636.

Boyd et al., 1988, "Determination of the Levels of Urokinae and Its Receptor in Human Colon Carcinoma Cell Lines", *Cancer Res.* 48:3112–3116.

Nielsen et al., 1988, "A 55,000–60,000 $M_r$ Receptor Protein for Urokinase–type Plasminogen Activator", *J. Biol. Chem.* 263:2358–2363.

Appella et al., 1987, "The Receptor–binding Sequence of Urokinase", *J. Biol. Chem.* 262:4437–4440.

Needham et al., 1987, "Binding of Urokinase to Specific Receptor Sites of Human Breast Cancer Membranes", *Br. J. Cancer* 55:13–16.

Miggnatti et al., 1986, "Tumor Invation through the Human Amniotic Membrane: Requirement for a Proteinase Cascade", *Cell* 47:487–498.

Plow et al., 1986, "The Plasminogen System and Cell Surfaces: Evidence for Plasminogen and Urokinase Receptors on the Same Cell Type", *J. Cell Biol.* 103:2411–2420.

Bajpai et al., 1985, "Urokinase Binding Sites on Human Foreskin Cells. Evidence for Occupancy with Endogenous Urokinase", *Biochem. Biophys. Res. Commun.* 133:994–1000.

Danø et al., 1985, "Plasminogen Activators, Tissue Degradation, and Cancer", *Adv. Cancer Res.* 44:139–266.

Stoppelli et al., 1985, Differentiation–Enhanced Binding of the Amino–Terminal Fragment of Human uokinase Plasminogen Activator to a Specific Receptor on U937 Monocytes, *Proc. Natl. Acad. Sci. USA* 82:4939–4943.

Vassalli et al., 1985, "A Cellular Binding SIte for the $M_r$ 55,000 Form of the Human Plasminogen Activato, Urokinase", *J. Cell Biol.* 100:86–92.

Werb et al., 1977, "Endogenous Activation of Latent Collagenase by Rheumatoid Synovial Cells", N. Eng. J. Med. 296:1017–1023.

Robbins. 1970, "Human Plasmin", *Meth. Enzymol.* 80:379–387.

\* cited by examiner

TARGETING VECTOR TO THE UROKINASE PLASMINOGEN ACTIVATOR RECEPTOR

BACKGROUND OF INVENTION

Urokinase plasminogen activator (uPA) is expressed in all mammalian species. It is produced by many cultured cell types of neoplastic origin and has been found more abundantly in explants of tumor tissue than in the corresponding normal tissue. uPA and its receptor, urokinase plasminogen activator receptor (uPAR), have been identified in extracts from human lung, colon, endometrial, breast, prostate and renal carcinomas, human melanomas, murine mammary tumors, the murine Lewis lung tumor, in ascites from human peritoneal carcinomatosis and human fibroblasts (Stopelli et al, *Proc. Natl Acad. Sci. USA*, 82:4939–43 (1985); Vassalli et al., *J. Cell. Biol.* 100:86–92(1985), Plow et al., *J. Cell. Biol.* 103:2411–2420 (1986), Boyd et al, *Cancer Res.*, 48:3112–6 (1988); Nielsen et al., *J. Biol. Chem.*, 263:2358–2363 (1988); Bajpai and Baker, *Biochem. Biophys. Res. Commun.*, 133:994–1000 (1985); Needham et al., *Br. J. Cancer*, 55:13–16 (1987)).

uPA has been identified as the initiator of a major amplified cascade of extracellular proteolysis and/or cell migration, presumably through a breakdown of the extracellular matrix, caused by plasmin together with other proteolytic enzymes. This cascade, when regulated, is vital to certain normal physiological processes but, when dysregulated, is strongly linked to pathological processes, such as cell invasion and metastasis in cancer. Dano et al., *Adv. Cancer Res.* 44:139–266 (1985). There have also been reports that uPA plays a role in (1) the degradative phase of inflammation, (2) the interference of lymphocyte-mediated cytotoxicity against a variety of cells, (3) angiogenesis, (4) endothelial cell migration which is important in tumor growth, and (5) in the cytotoxic effect of natural killer cells.

uPA is a multidomain serine protease comprising (1) an N-terminal epidermal growth factor-like domain, (2) a kringle domain, and (3) a C-terminal serine protease domain. The single chain pro-uPA is activated by plasmin, which cleaves the chain into the disulfide-linked two chain active form.

The cellular receptor for uPA is uPAR, which is a multidomain protein that is anchored by a glycolipid to the cell membrane, thus ensuring that activation of uPA is a pericellular event. Behrendt et al., *Biol. Chem.*, 376:269–79 (1995). uPAR binds the active uPA, as well as pro-uPA and uPA bound to an inhibitor molecule DFP which binds to uPA's active site. While the receptor binding domain of uPA has been localized to amino acids in the N-terminal growth factor-like domain region, there are varying studies which have yielded differing results regarding the span of the receptor binding domain.

For example, Stopelli et al. (*Proc. Natl. Acad. Sci. USA*, 82:4939–43 (1985)) first reported that the N-terminal fragment of uPA (amino acids 1–135) was sufficient for high affinity, sub-nanomolar binding to uPAR. Further work confined the uPAR binding domain to amino acids 1–48 (Robbiati et al., *Fibrinolysis*, 4:53–60 (1990)). Dano et al. showed that a region spanning amino acids 12–32 could block the binding of the full-length wild-type uPA to uPAR (published PCT application WO 90/12091). Other studies have shown that residues 20–30 confer the specificity of binding, but that residues 13–19 are also needed to attain the proper binding confirmation (Appella et al., *J. Biol. Chem.*, 262:4437–40 (1987). Correspondingly, studies have shown that residues 20–30 can inhibit the binding of full-length uPA to uPAR but that a longer peptide comprising residues 17–34 is significantly more potent, requiring 10-fold less to achieve the same result. Kobayashi et al., *J. Cancer*, 57:727–33 (1994). Quax et al. (*Arterioscler. Thromb. Vasc. Biol.*, 18:693–701 (1998) have reported that the receptor binding domain of uPA is localized between amino acids 20–32. In addition, Jones et al., in U.S. Pat. No. 5,942,492 have shown that cyclic peptides comprising residues 20–30 are sufficient to bind uPAR and act as antagonists of binding of uPA to uPAR and that residues N-terminal to residue 20 and C-terminal to residue 30 are not essential for high affinity binding. In view of these studies, the precise location of the uPAR high specificity binding domain in uPA is unclear.

The activity of uPA, when bound to uPAR, is confined to the cell surface by plasminogen activator inhibitors (PAI-1 and PAI-2), which bind to and inactivate the uPAR bound uPA. This tight control of uPA activity is necessary because uPA acts upon a substrate, plasminogen, that is present at a high concentration in plasma. Robbins, *Meth. Ensemble.*, 19:184–99 (1970). uPA's action on plasminogen produces plasmin which is a powerful broad spectrum protease that not only degrades extracellular matrix proteins directly, but also activates the latent forms of other proteases, including several metalloproteases. Werb et al., *N. Eng. J. Med.*, 296:1017–1023 (1977); Mignatti et al., *Cell*, 47:487–98 (1986); He et al., *Proc. Natl. Acad. Sci. USA*, 86:2632–36 (1989); and Martrisian, *Bioessays*, 14:455–63 (1992).

In tumor biology, the link between extracelluar proteolysis and angiogenesis is clearly evident. Break-up and dissolution of existing extracellular matrix is necessary in order to create new space for blood vessels to grow into. The processes of proteolysis and angiogenesis are highly coordinated. For example, two angiogenic growth factors, basic fibroblast growth factor and vascular endothelial growth factor markedly up-regulate the production of uPA and the expression of uPAR by endothelial cells. Mignatti et al. *J. Cell. Biol.*, 113:1193–1201 (1991); Mandriota et al, *J. Biol. Chem.*, 270:9709–9716 (1995). Therefore, uPA and uPAR have emerged as a target for developing an anti-metastatic/anti-angiogenic therapy for cancer. Fazioli et al, *Trends Pharmacological Sci.*, 15:25–29 (1994).

The uPA/uPAR interaction goes far beyond localizing proteolysis at the cell surface however. The mere occupation of uPAR by uPA induces, by indirect means, signal transduction events leading to one or more of the following effects: mitogenesis (Rabbani et al., *J. Biol. Chem.*, 267:14151–56 (1992)); expression of the c-fos gene (Dumler et al., *FEBS Lett.*, 322:37–40 (1994)); cysteine- and metalloprotease expression by macrophages (Rao et al, *J. Clin. Invest.*, 96:465–74 (1995)); transfer of mechanical force leading to increased cytoskeletal stiffness (Wang et al., *Am. J. Physiol.*, 268:C1062–66 (1995)); endothelial cell migration (Odekon et al., *J. Cellul. Physiol.*, 150:258–63 (1992)); endothelial cell morphogenesis into tubular structures (Schnaper et al., *J. Cellul. Physiol.*, 165:101–118 (1995)); and endothelial cell deformability and motility (Lu et al., *FEBS Lett.* 380:21–24 (1996). All of these phenomenon are blocked by blocking the access of uPA to uPAR.

In addition to binding uPA, uPAR serves as a cellular adhesion receptor for vitronectin and as a signaling receptor. Wei et al., *J. Biol. Chem.*, 269:32380–88 (1994); Robinson, *Signal transduction via GPI-anchored membrane proteins. ADP ribosylation in animal tissue.* Plenum Press, NY (1997); Wei et al., *J. Cell. Biol.*, 144:1285–1294 (1999). uPAR also interacts with several cell surface proteins including integrins, low-density lipoprotein receptor-related peptide, very-low-density lipoprotein receptor, megalin and the mannose-6-phosphate/insulin-like growth factor-II receptor. Moestrup et al., *J. Biol. Chem.*, 268:16564–70 (1993); Heegaard et al, *J. Biol. Chem.*, 270:20855–61 (1995); Czekay et al., *Mol. Biol. Cell,* 8:517–32 (1997).

uPAR is further involved in both clathrin-dependent and clathrin-independent endocytosis. Vilhardt et al., *Mol. Biol. Cell,* 10:179–195 (1999). Clatherin-dependent endocytosis of uPAR is believed to depend on binding of uPA:PAI-1 to uPAR and subsequent interaction with internalization receptors for the low-density lipoprotein receptor family, which are internalized through clathrin-coated pits. This interaction is inhibited by receptor-associated protein (RAP). In contrast, clathrin independent endocytosis of uPAR, which is also believed to occur when uPA:PAI-1 is bound, is not inhibited by RAP. See Vilhardt et al., *Mol. Biol. Cell,* 10:179–195 (1999).

Rodenberg et al. (*Biochem J.,* 329:55–63 (1998)) have shown that endocytosis of uPA requires both uPA and PAI-1. The complex of uPA and PAI-1 has been shown to be required for binding to the endocytosis receptors α2-macroglobulin receptor/low-density lipoprotein receptor-related protein (α2MR/LRP) and very-low-density lipoprotein receptor (VLDLR) while free uPA and PAI-1 are not able to bind to the endocytosis receptors. See Rodenberg et al., *Biochem J.,* 329:55–63 (1998).

The region of uPA which appears to be responsible for its binding to PAI-1 has been localized to the C-terminal proteinase domain of uPA. Wei et al., *J. Biol. Chem.,* 269:32380–8 (1994); Stoppelli et al., *Proc. Natl. Acad. Sci. USA,* 82:4939–43 (1985); Conese and Blasi, *Biological and Chemical Hope-Seyler,* 376:143–55 (1995). In addition, Rodenberg et al. have isolated a four residue region of PAI-1 which appears to be responsible for the high affinity binding of the uPA:PAI-1 complex to the endocytosis receptors. These references have suggested that endocytosis of uPA is dependent on PAI-1. Furthermore, the endocytosis of uPA has also been shown to be dependent upon uPAR. Goretzki and Mueller, *J. Ce. Sci.* 110:1395–402 (1997).

The effective treatment of inherited and acquired disorders through the delivery of a transgene which is capable of correcting the disorder is dependent upon the efficiency of delivery of the transgene. Various vector systems have been developed that are capable of delivering a transgene to a target cell. However, there remains a need to improve the efficiency of transgene delivery to achieve effective treatments. Improved efficiency is desirable to both increase the ability of the vector to correct the cellular defect and to decrease the toxic effects of the vector by decreasing the required amount of the vector to achieve effective treatments.

Adenovirus is a non-enveloped, nuclear DNA virus with a genome of about 36 kb. See generally, Horwitz, M. S., "Adenoviridae and Their Replication," in *Virology,* 2nd edition, Fields et al., eds., Raven Press, New York, 1990. Recombinant adenoviruses have advantages for use as delivery systems for nucleic acid molecules coding for, inter alia, proteins, ribozymes, RNAs, antisense RNA that are foreign to the adenovirus carrier (i.e. a transgene), including tropism for both dividing and non-dividing cells, minimal pathogenic potential, ability to replicate to high titer for preparation of vector stocks, and the potential to carry large inserts. See Berkner, K. L., 1992, *Curr. Top. Micro Immunol,* 158:39–66; Jolly D., 1994, *Cancer Gene Therapy,* 1:51–64.

Adenoviruses have a natural tropism for respiratory tract cells which has made them attractive vectors for use in delivery of genes to respiratory tract cells. For example, adenovirus vectors have been and are being designed for use in the treatment of certain diseases, such as cystic fibrosis (CF): the most common autosomal recessive disease in Caucasians. In CF, mutations in the cystic fibrosis transmembrane conductance regulator (CFTR) gene disturb cAMP-regulated chloride channel function, resulting in pulmonary dysfunction. The gene mutations have been found to encode altered CFTR proteins which cannot be translocated to the cell membrane for proper functioning. The CFTR gene has been introduced into adenovirus vectors to treat CF in several animal models and human patients. Particularly, studies have shown that adenovirus vectors are fully capable of delivering CFTR to airway epithelia of CF patients, as well as airway epithelia of cotton rats and primates. See e.g., Zabner et al., *Nature Genetics* 6:75–83 (1994); Rich et al., *Human Gene Therapy* 4:461–476 (1993); Zabner et al., *Cell* 75:207–216 (1993); Crystal et al., *Nature Genetics* 8:42–51 (1994).

However, it would be useful to alter the tropism of a virus, such as adenovirus, to allow it to be used to deliver a nucleic acid molecule to a variety of cells for which the virus is normally non-tropic and to improve the uptake of the virus into cells.

Certain situations exist where it would be useful to modify the tropism of viruses (such as adenovirus, adeno-associated virus, retrovirus, etc.) to target the vector to cell surface molecules other than the virus' normal cell surface receptor. For example, certain cells are normally refractory to infection by certain viruses. It would be useful to have a method of overcoming the inability of these cells to be infected. Similarly, in cancer cells, many receptors are up-regulated, such as uPAR. Therefore, it would be useful to be able to specifically target vectors to these up-regulated receptors to increase the uptake of nucleic acids providing for antitumor agents for treatment of such cancers.

Furthermore, in practice, in order to achieve effective transfer of viral vectors into affected cells, repeated administration of the viral vector over a course of time may be required. Readministration of the viral vector can trigger an immune response within the subject to whom the vector is given, which requires subsequently higher doses of the viral vector to avoid immune elimination of the virus. If the efficiency of uptake of the viral vector is increased, a lower dose of the vector can be used, which, in turn, may help alleviate the immune response problems which are associated with the readministration of viral vectors. Similar problems may also be alleviated for other types of vectors as well, such as RNA, polynucleotides, small molecules, etc.

Administration of the cystic fibrosis transmembrane conductance regulator (CFTR) cDNA to airway epithelia could provide an important new treatment for cystic fibrosis (CF) lung disease. However, despite the demonstrated ability of several vectors to deliver and express CFTR and correct the Cl$^-$ channel defect in airway epithelia in vitro and in vivo (see O'Neal and Beaudet. *Hum Mo. Genet.* 3:1497–1502 (1994); Crystal. *Science* 270:404–10 (1995); Wilson. *New England J. Med.* 334:1185–7 (1996); Middleton and Alton. *Thorax* 53:197–9 (1998); and Welsh. *J. Clin. Invest.* 105:589–596 (2000), for review)), a severe inefficiency in delivering a vector coding for CFTR has impeded the clinical development of the administration of CFTR to CF patients as a new treatment. The two most important factors for the inefficiency are limited binding of vector to the apical surface of differentiated human airway epithelia and limited endocytosis across the apical membrane. A paucity of apical receptors prevents binding of viral vectors, including adenovirus (Bergelson et al. *Science* 275:1320–23 (1997); Pickles et al. *J. Virol.* 72:6014–23 (1998); Walters et al. *J. Biol. Chem.* 274:10219–10226(1999)), adenovirus-associated virus Teramato et al. *J. Virol.* 72:8904–8912 (1998); Summerford and Samulski. *J. Virol.* 72:1438–45 (1998); Duan et al. *Hum. Gene Ther.* 9:2761–76 (1998), and retroviral vectors (Wang et al. *J. Virol.* 72:9818–26 (1998), as well as nonviral vectors, including cationic lipids (Zabner et al. *J. Biol. Chem.* 270:18997–19007 (1995); Matsui et al. *J. Biol. Chem.* 272:1117–26 (1997); Fasbender et al. *Gene Ther.* 4:1173–80 (1997)). Compounding the limited vector binding, and in contrast to observations in cell lines, the rate of endocytosis across the apical membrane of differentiated airway epithelia is low and may limit administration of adenovirus, AAV, retrovirus and nonviral vectors. Pickles et al. *J. Virol.* 72:6014–23 (1998); Fasbender et al. *Gene Ther.* 4:1173–80 (1997); and Goldman and Wilson. *J. Virol.* 69:5951–8 (1995).

Hence, a method that increases vector binding and endocytosis may enhance both viral and non-viral vector administration to airway epithelia. One strategy to circumvent the lack of apical receptors is to non-specifically increase vector biding. For example, earlier work showed enhanced administration of adenovirus or AAV by incorporating virus in calcium phosphate (CaPi) coprecipitate. See Fasbender et al. *J. Clin. Invest.* 102:184–93 (1998); Lee et al. *Hum. Gene Ther.* 10:603–13 (1999); Walters et al. *J. Virol.* 74:535–540 (2000). However, this delivery method did not increase endocytosis across the apical surface. See Walters and Welsh, *Gene Ther.* 6:1845–1850 (1999); U.S. patent application Ser. No. 09/082,510 (incorporated herein by reference).

Other vectors comprising cationic amphiphiles such as lipids, synthetic polyamino polymers (Goldman et al., 1997, *Nat. Biotechnol.* 15:462–466), and poly-lysine (Kollen et al., 1996, *Hum. Gene. Ther.* 7:1577–1586), which are used with nucleic acid molecules, such as a plasmid, to transfect a target cell, are useful for delivery of nucleic acids to cells. Most of these vectors suffer from nonspecificity and inefficiency of delivery. Therefore, a method for targeting these systems to cells and improving the uptake of such vectors into cells would also be useful.

U.S. Pat. No. 5,759,452 ('452 patent) discloses the use of an isolated portion of the A-chain of a urokinase-type plasminogen activator linked to a "drug", wherein the A-chain portion binds stably to an outer membrane of a platelet and delivers the drug to the platelet. The portion of the A-chain comprises amino acids 1 through 132 or can be the full-length urokinase-type plasminogen activator. The '452 patent disclosure is limited to the delivery of a "drug" via the urokinase-type plasminogen activator in platelets and does not provide teaching for the delivery to other cell-types, including airway epithelia, and does not provide teaching for the improved uptake of a vector (including a small molecule, protein, polynucleotide, RNA, DNA, virus, viral vector, plasmid, etc) to various cell types.

PCT Patent Application WO/9846632 discloses cyclic uPAR inhibitor peptides derived from uPA amino acids sequences 22–28 which bind to uPAR and block the binding of uPA. WO/9846632 describes the use of these peptides for the delivery of diagnostic markers or therapeutic agents to uPAR-expressing cells. WO/9846632 states that linear and cyclic peptides corresponding to amino acids 19–31 of uPA display a surprisingly higher affinity for uPAR than previously described peptides spanning amino acids 14–32 of uPA (Magdolen et al., *Eur. J. Biochem.* 237:743–751 (1996) and 13–19 of uPA (Appella et al., *J. Biol. Chem.* 262:4437–4440 (1987) which display a low affinity with uPAR. The low affinity of the peptides described by Magdolen et al. and Appella et al. are described as not being sufficient for therapeutic use creating a need for uPA peptides which feature higher affinity for the uPAR receptor.

The present invention is based in part on the unexpected finding that the seven residue peptide of uPA (corresponding to residues 13–19described by Appella et al. as a low affinity uPAR binder, is capable of high affinity binding and facilitating the delivery and endocytosis of the peptide, including the peptide linked to virus (and other cargo) by a cell bearing uPAR, even though this region of uPA does not bind PAI-1 which has previously been shown a necessary factor for the endocytosis of uPA. In addition, the present invention is also based on the previously unknown finding that airway epithelial cells express uPAR and that uPA is capable of binding thereto and facilitating endocytosis therein.

These findings have allowed for the targeted and improved delivery of adenovirus vectors to airway epithelia and is also useful for the targeted and improved delivery of cargo in general to various cell types expressing uPAR.

SUMMARY OF THE INVENTION

The present invention relates to the targeted delivery of a delivery vehicle construct which specifically binds to and stimulates endocytosis into cells expressing the urokinase plasminogen activator receptor (uPAR), and in particular, human airway epithelia. The delivery vehicle construct comprises a portion of uPA and a cargo linked thereto. The delivery vehicle construct is useful for the targeted delivery of cargo, including inter alia, small molecules, polynucleotides (coding, inter alia, for a protein, RNA, ribozyme, or antisense RNA), DNA, oligonucleotide decoys, antisense RNA, polypeptides, viruses, modified viruses, viral and non-viral vectors and plasmids, to cells expressing uPAR, and in particular, human airway epithelia. Preferred viruses, modified viruses and viral vectors are derived from adenovirus, retrovirus, herpes simplex virus, adeno-associated virus or poxvirus, with adenovirus being particularly preferred.

In one aspect of the invention, the uPA portion of the delivery vehicle construct comprises the full-length, wild-type uPA or a fragment of uPA which has the PAI-1 binding region deleted and is useful for the targeted delivery of the cargo to airway epithelia.

In a preferred aspect of the invention, the uPA portion of the vector is a seven residue peptide derived from uPA (u7-peptide) comprising amino acids 13–19 of uPA (amino acids CLNGGTC; SEQ ID NO:1, where C is Cysteine, L is Leucine, N is Asparagine, G is Glycine, and T is Threonine) and the cargo portion is an adenoviral vector, preferably containing a transgene. In a particularly preferred embodiment of the invention, the uPA portion of the vector is the u7-peptide, the cargo is an adenoviral vector containing DNA coding for CFTR and the vector is delivered to airway epithelia lacking a functional CFTR gene.

The present invention also provides a method for delivering the delivery vehicle construct to a target cell. The method comprises (a) contacting a target cell with a delivery vehicle construct comprising a uPA portion and a cargo portion; (b) delivering the cargo to the cell; and (c) producing a desired result in the cell. Such desired result may include, inter alia, the correction of a defect in the target cell (e.g. correction of a Cl− channel in the target cell with a transgene encoding CFTR) the destruction of the target cell (e.g. destruction of a cancerous cell with a suicide gene), or the delivery of a gene to the target cell.

DETAILED DESCRIPTION

The delivery vehicle constructs of the present invention comprise a uPA portion and a cargo portion and can enable the delivery of the cargo (e.g. small molecules; transgenes; polynucleotides, which may code for a protein, RNA, ribozyme, or antisense RNA; DNA; oligonucleotide decoys; antisense RNA; polypeptides; viruses; modified viruses; viral and non-viral vectors; and plasmids) to and uptake by cells. The cargo may comprise a transgene, such as CFTR, which is capable of correcting an inherited or acquired disorder in a subject to which it is administered.

Typically the delivery vehicle carries a transgene which, as defined herein, refers to a nucleic acid molecule not normally present in the vector that codes for, inter alia, a protein, RNA, ribozyme, antisense RNA. Examples of transgenes include, but are not limited to, CFTR, α-1-antitrypsin AAT, β-glucocerebrosidase, or suicide gene products (suicide gene products may include, inter alia, HSV thymidine kinase (TK), modified TK, cystine deaminase, *E. coli* nitroreductase, xanthine-guanine phosphoribosyl transferase, mammalian Pf50 2B1, purine nucleoside, phosphorylase, thymidine phosphorylase, deoxycytidine kinase and Varicella Zoster virus TK). In a preferred embodiment, the delivery vehicle construct of the present invention comprises the u7 peptide of uPA (SEQ ID NO:1) and an adenoviral vector containing a transgene. In a particularly preferred embodiment, the delivery vehicle construct of the present invention comprises the u7 peptide, an adenoviral vector encoding CFTR and is administered to airway epithelia.

Figure 1:
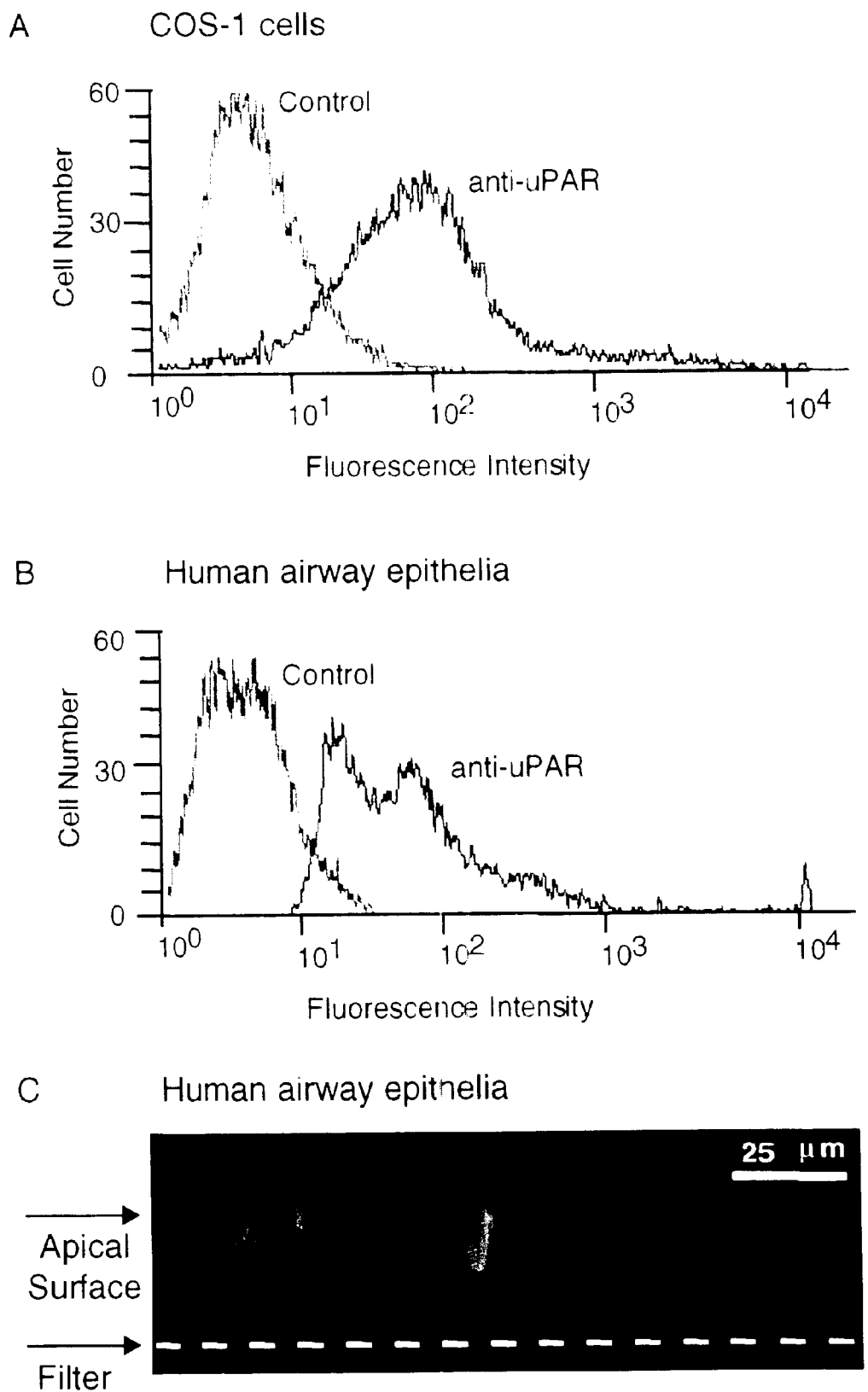
FIGS. 1a–c: Expression of uPAR in differentiated human airway epithelia. (A) FACS analysis of uPAR staining in COS-1 cells (B) and differentiated human airway epithelia. (C) Projection of 180 µm thick X-Z series of confocal images. Green is staining from anti-uPAR antibody and red is ethidium bromide fluorescence to identify cells.
Figure 2:
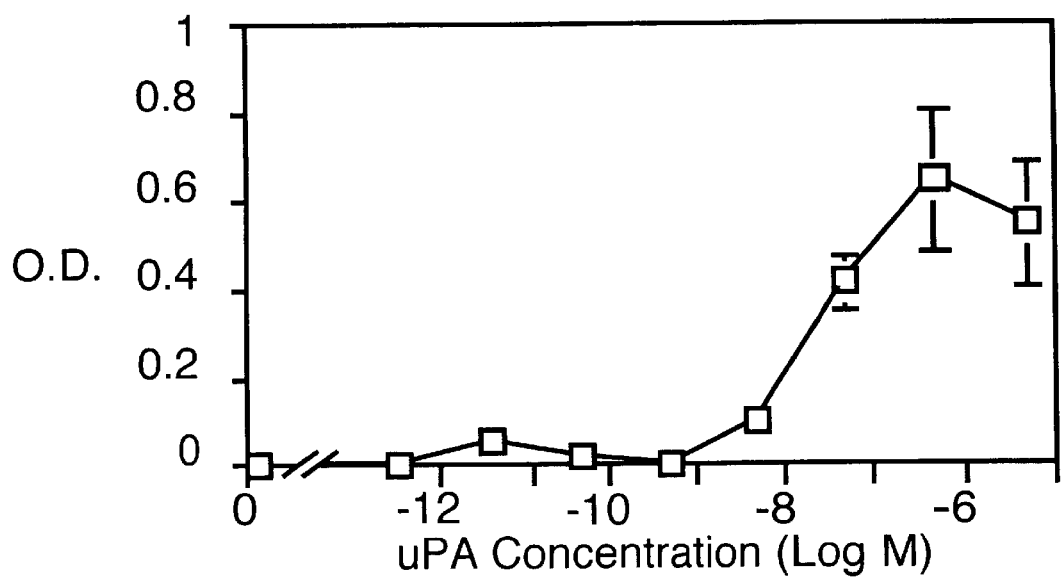
FIG. 2: Concentration-dependent binding of uPA to differentiated human airway epithelia. Data are optical density at 450 nM (O.D.) indicating color change in ELISA assay. n=5.
Figure 3:
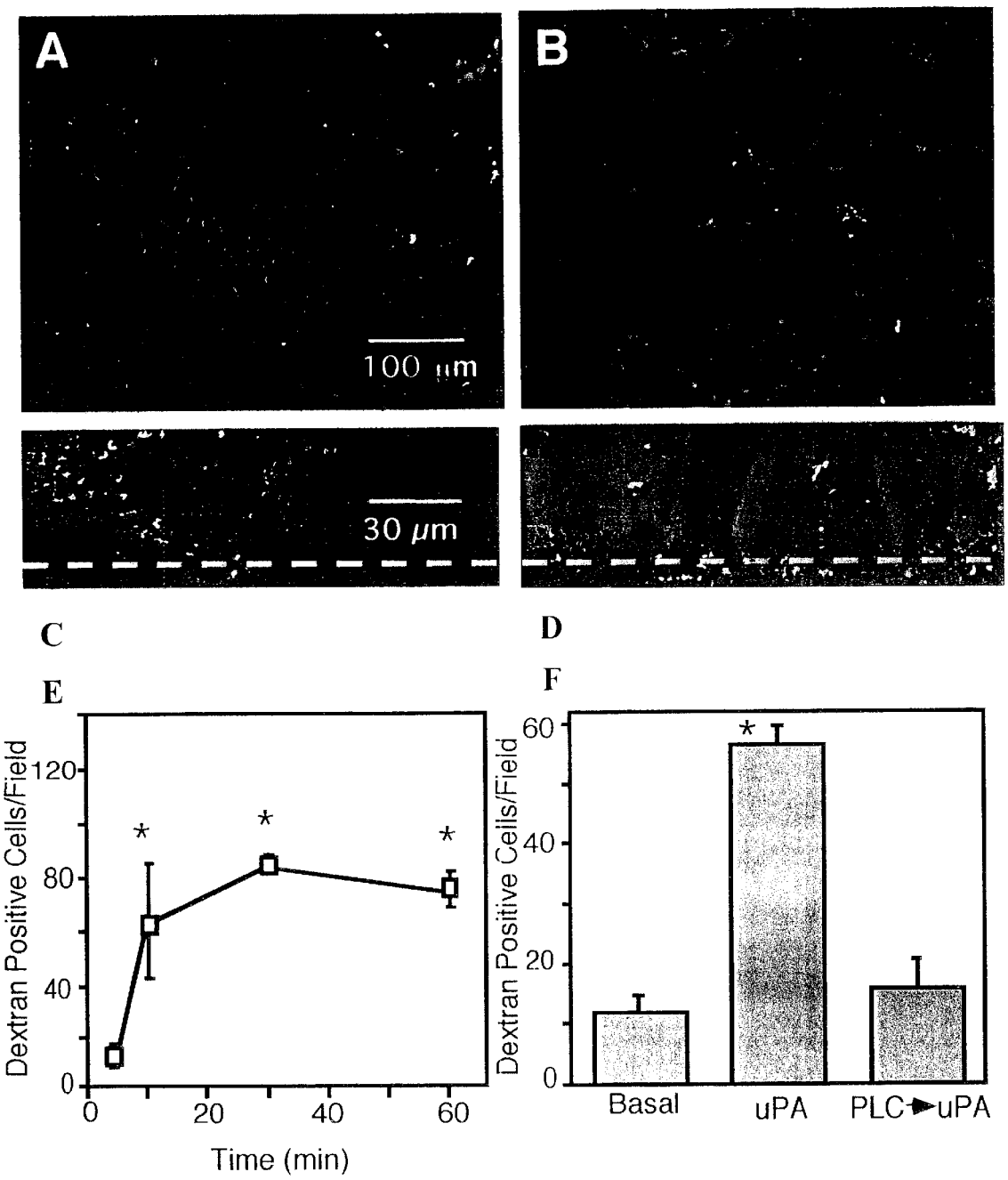
FIG. 3: uPA stimulation of fluid phase endocytosis by differentiated human airway epithelia measured as uptake of Texas Red dextran. En face images (Panels A and B) and confocal X–Z series (Panels C and D) of labeled dextran uptake under basal conditions (A and C) and following application of 50 nM uPA (B and D). Dashed line indicates filter. (Panel E) Time-course of dextran uptake following application of uPA (59 nM). (D) (Panel F) Graph shows the effect of PI-PLC on uPA-mediated stimulation of dextran uptake. n=10. Asterisk indicates $p \leq 0.05$.
Figure 4:
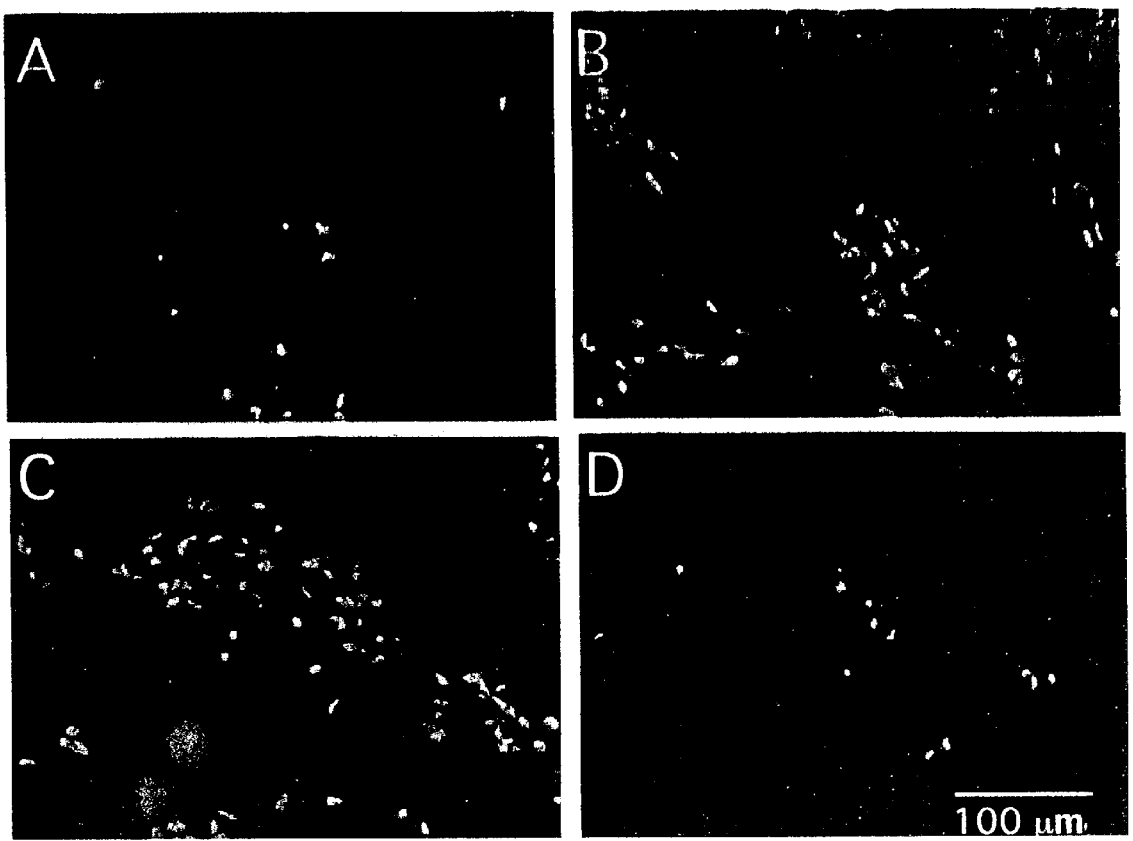
FIG. 4: Apical fluid phase endocytosis by human airway epithelia stimulated by uPA and u7-peptide (SEQ ID NO:1). Data are en face images showing Texas-Red dextran uptake. Panels are basal endocytosis (Panel A), endocytosis following apical application of 50 nM uPA (Panel B), 0.15 µM u7-peptide (Panel C), or 0.15 µM scrambled u7-peptide (SEQ ID NO:2). (Panel D). Effect of uPA and peptides on a number of cells showing endocytosis (Panel E). n=5. Asterisk indicates $p \leq 0.05$.
Figure 4:
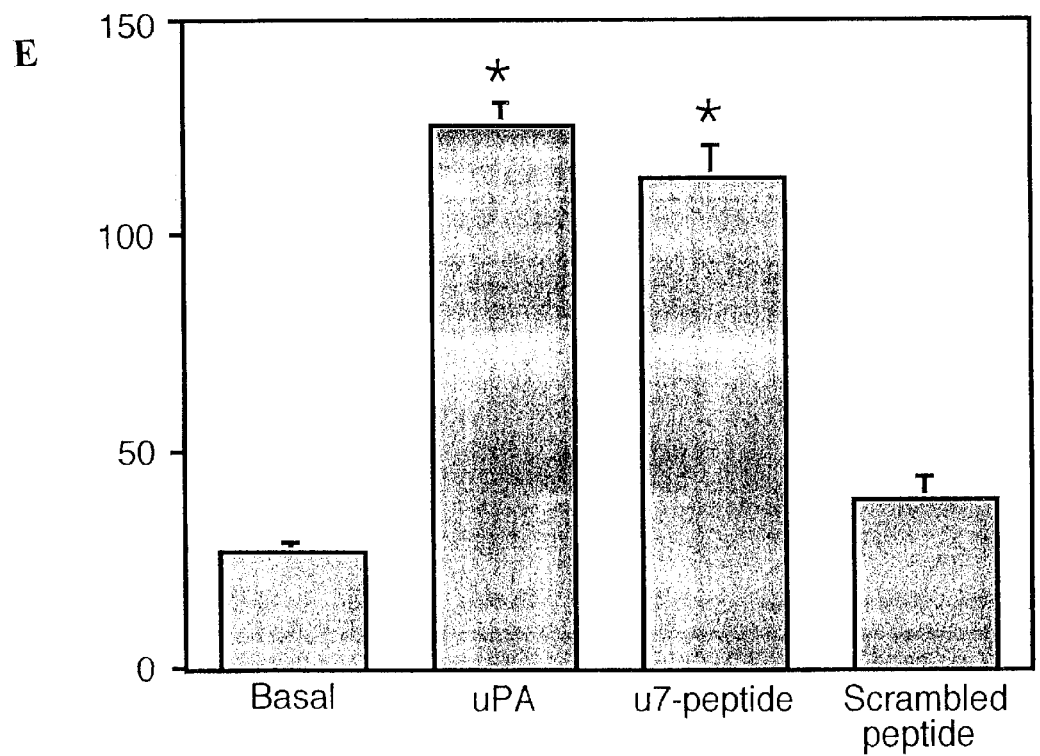
Figure 5:
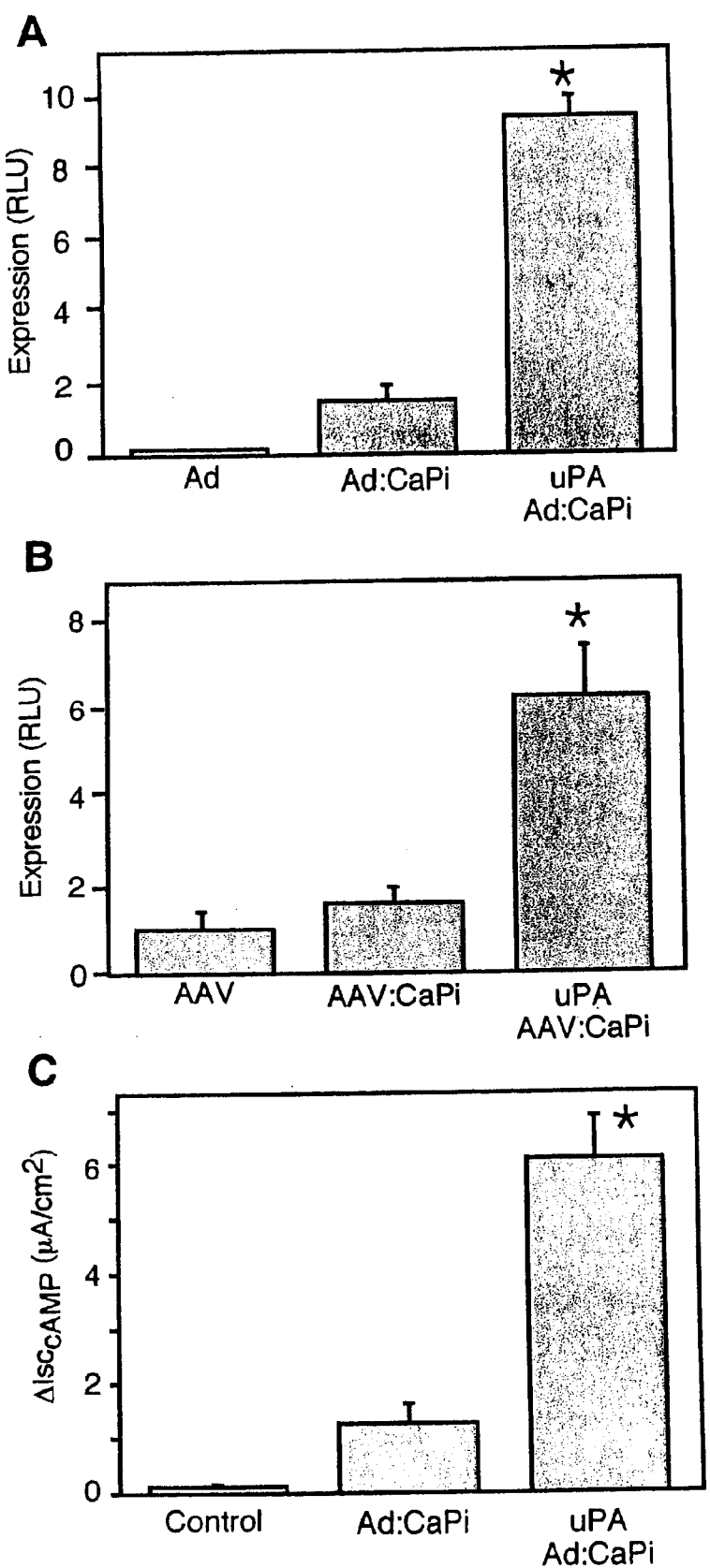
FIGS. 5a–c: uPA stimulation of gene transfer to normal and CF airway epithelia. (a) Apical application of uPA (50 nM) prior to infection with Ad2/βGal-4 in a CaPi co-precipitate (n=4). (B) Apical application of uPA (50 nM) prior to infection with recombinant AAV in a CaPi co-precipitate (n=10). (C) cAMP-stimulated increase in short-circuit current (ΔIsc) in CF airway epithelia treated with Ad2/CFTR-16 delivered in a CaPi coprecipitate (n=4). Asterisk indicates $p \leq 0.05$.
Figure 6:
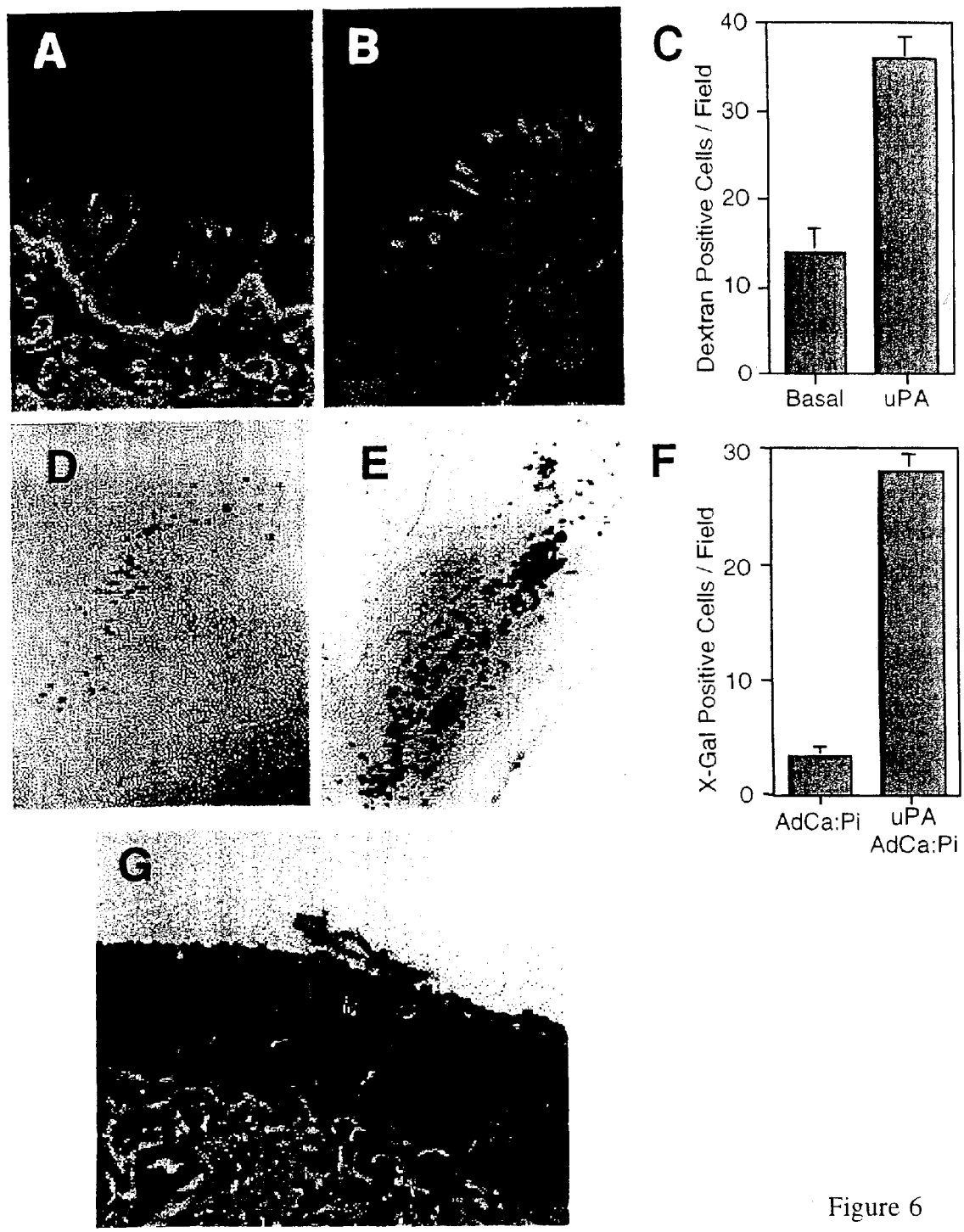
FIGS. 6a–g: Endocytosis and gene transfer to freshly excised monkey tracheal explants. (A) Fluid phase endocytosis measured as uptake of FITC-dextran under basal conditions, or (B) following addition of 50 nM uPA; trachea shows significant background fluorescence. (c) Quantitation of endocytosis (n=12). (D) X-gal stained explants infected with Ad:CaPi coprecipitates alone or (E) following treatment with 50 nM uPA. (F) Quantitation of gene transfer (n=4). (G) Thin section of X-gal stained uPA treated explant. Asterisks indicate $p \leq 0.05$.

The methods of the present invention enable the delivery vehicle construct to be specifically targeted to a cell expressing uPAR on its surface via the binding of the delivery vehicle construct to uPAR cell surface molecules. FIG. 1 shows the expression of uPAR in human airway epithelia. FIG. 2 shows the concentration dependent binding of uPA to differentiated human airway epithelia and demonstrates that human airway epithelia, which express uPAR on their cell surface, are capable of binding to uPA. It has been discovered by the present inventors that, after binding to the uPAR cell surface molecule of human airway epithelia, uPA is endocytosed by the cell. See FIG. 3 and FIG. 4. In addition, it has been discovered that the delivery vehicle of the present invention comprising a uPA portion and a cargo portion also binds to and is endocytosed by airway epithelia. See FIG. 5, FIG. 6 and FIG. 7.

The cargo portion of the present invention may comprise any virus or viral vector known to be useful in the art. Examples of such viral cargo include: Adenoviridae; Birnaviridae; Bunyaviridae; Caliciviridae, Capillovirus group; Carlavirus group; Carmovirus virus group; Group Caulimovirus; Closterovirus Group; Commelina yellow mottle virus group; Comovirus virus group; Coronaviridae; PM2 phage group; Corcicoviridae; Group Cryptic virus; group Cryptovirus; Cucumovirus virus group Family Φ6 phage group; Cysioviridae; Group Carnation ringspot; Dianthovirus virus group; Group Broad bean wilt; Fabavirus virus group; Filoviridae; Flaviviridae; Furovirus group; Group Germinivirus; Group Giardiavirus; Hepadnaviridae; Herpesviridae; Hordeivirus virus group; Illarvirus virus group; Inoviridae; Iridoviridae; Leviviridae; Lipothrixviridae; Luteovirus group; Marafivirus virus group; Maize chlorotic dwarf virus group; icroviridae; Myoviridae; Necrovirus group; Nepovirus virus group; Nodaviridae; Orthomyxoviridae; Papovaviridae; Paramyxoviridae; Parsnip yellow fleck virus group; Partitiviridae; Parvoviridae; Pea enation mosaic virus group; Phycodnaviridae; Picomaviridae; Plasmaviridae; Prodoviridae; Polydnaviridae; Potexvirus group; Potyvirus; Poxviridae; Reoviridae; Retroviridae; Rhabdoviridae; Group Rhizidiovirus; Siphoviridae; Sobemovirus group; SSV1-Type Phages; Tectiviridae; Tenuivirus; Tetraviridae; Group Tobamovirus; Group Tobravirus; Togaviridae; Group Tombusvirus; Group Torovirus; Totiviridae; Group Tymovirus; Plant virus satellites.

Additionally, cargo include, but are not limited to, lipid vehicles, poly-lysine vehicles, synthetic polyamino polymer vehicles, and modified viral vehicles which are used with nucleic acid molecules, such as a plasmid comprising a transgene.

Particularly preferred cargo are those cargo which have been previously employed for the delivery of transgenes, including, for example, adenovirus, adeno-associated virus, retrovirus, herpes virus and poxvirus. In a preferred embodiment, the cargo is adenovirus. Normally, adenoviruses bind to a cell surface receptor (CAR) of susceptible cells via the knob domain of the fiber protein on the adenovirus surface. A secondary method of entry for adenovirus is through integrins present on the cell surface through Arginine-Glycine-Aspartic Acid (RGD) sequences of the adenoviral penton base protein. The present invention utilizes a delivery vehicle construct which may comprise an adenovirus portion and a uPA portion. The uPA portion of the delivery vehicle construct of the present invention allows for improved entry of the adenovirus portion to a target cell.

In another embodiment of the present invention, the cargo of the delivery vehicle construct is a retrovirus. Retroviruses normally bind to a species specific cell surface receptor (e.g., CD4, CAT, RAM1/GLVR2, GLVR1 and GALV). However, if the cells of interest do not have such surface receptors, the virus can not infect such cells. The method of the present invention allows the infection of normally refractory cells with a retrovirus of interest.

Another viral cargo which may be employed in the present invention is adeno-associated virus (AAV). AAV vectors are useful for the delivery of transgenes to cells because they allow for stable integration of transgenes into a target cell and they infect a range of cells. The inherent infection pathway of AAV vectors may be blocked by pre-incubation with neuraminidase. Once the inherent infection pathway is inhibited, only those cells expressing uPAR on the cell surface will be infected by the delivery vehicle construct of the present invention comprising AAV. This would create a delivery vehicle construct that would limit the complication of delivery of a transgene into cells other than the target cells. If the objective is to deliver a suicide gene to cancer cells by using the delivery vehicle of the present invention, such a targeted delivery system is particularly desired to avoid destruction of otherwise healthy cells.

The cargo portion also may include, but is not limited to, small molecules, polynucleotides, DNA, oligonucleotide decoys, RNA, antisense RNA, polypeptides, nonviral vectors and plasmids. Small molecules may be therapeutically useful and may include drugs or other agents which act to ensure proper functioning of a cell or molecules which may induce apoptosis or cell lysis, where death of a cell, such as a cancerous cell, is desired. Nucleic acids may code for, inter alia, a protein, RNA, ribozyme, or antisense RNA. The protein, RNA or ribozyme encoded by the nucleic acid may allow for the elimination of an undesired function of a molecule. Decoy oligonucleotides may contain specific binding sites for transcription factors and may block the function of the transcription factors in vitro and in vivo. Where the cargo is a polypeptide, the polypeptide may be a peptide or protein which, when delivered to the target cell, provides a desired function to the cell or induces a particular phenotypic alteration.

The uPA portion of the delivery vehicle construct of the present invention is "linked" to the cargo portion and facilitates the targeted cellular uptake of the cargo portion. As used herein, the term "link" refers to the connection of the uPA portion to the cargo portion which may be any covalent cross-linkage or non-covalent linkage or any other type of linkage which enables the uPA portion to facilitate delivery and uptake of the cargo portion to cells (e.g. a fusion protein comprising the peptide and another protein, the expression of the uPA portion on the surface of a viral vector, linkage of the uPA portion via chemical means to the cargo portion, etc.) wherein said linkage is between the uPA portion and the cargo portion of the present invention.

One type of linkage comprises a chemical linkage. Any type of chemical linkage as known in the art can be used, provided the chemical modification which creates the linkage does not affect the binding and subsequent endocytosis of the delivery vehicle to the target cell.

Additional linkers include polymers which may be chemically modified to be used as linkers. Polymers are large, non-immunogenic, biologically inert molecules comprising a chain of smaller molecules linked by covalent bonds. Polymers useful in accordance with the present invention are those which when used to covalently or noncovalently link the uPA portion and the cargo portion of the delivery vehicle construct of the present invention, provide a polymer-modified delivery vehicle construct that retains the ability to bind to and be endocytosed by the target cell. The polymers may be homopolymers or heteropolymers and may be linear or branched. Suitable polymers include polyalkalene compounds such as polyalkalene oxides and glycols, e.g. polyethylene glycol (PEG) or polypropylene glycol (PPG).

The uPA portion and the cargo portion may also be linked together by the creation of a fusion molecule. For example, if the cargo is a protein or a peptide, the uPA portion and the cargo portion may be expressed in a recombinant expression system, such as an *E. coli* expression system or a yeast expression system, as a fusion comprising the uPA portion and the cargo portion. Additionally, if the cargo is a peptide and the uPA portion is a peptide, the cargo portion and the uPA portion may be synthesized as a continuous peptide. Similar fusion constructs may be created where the cargo is either DNA or RNA.

As used herein, the uPA portion of the present invention comprises a portion of the urokinase plasminogen activator which is capable of binding to and facilitating endocytosis into a target cell. The uPA portion preferably does not include the C-terminal region of uPA responsible for the binding to PAI-1. In a particularly preferred embodiment, the uPA portion is the u7 peptide (SEQ ID NO:1) and is capable of binding to the cell surface receptor uPAR and facilitating endocytosis of the peptide, or any cargo linked thereto, into the target cell. Where the target cell is any cell expressing uPAR on its cell surface, the uPA portion is preferably the u7 peptide (SEQ ID NO:1). Where the target cell is airway epithelia, the uPA portion may include any portion of uPA capable of binding to and facilitating endocytosis into airway epithelia, including, but not limited to, full length wild-type uPA, the u7 peptide (SEQ ID NO:1), and uPA lacking the PAI-1 binding portion. Preferably, the uPA is human uPA.

The usefulness of the present invention may be demonstrated, for example, by incubating the delivery vehicle construct comprising a uPA portion linked to a cargo portion with target cells which express uPAR on the cell surface and measuring the efficiency of transfer of the uPA/cargo delivery vehicle construct into the target cell. The delivery vehicle construct is also useful to identify target cells which are susceptible to the transfer of the delivery vehicle construct of the present invention. Target cells may be identified by incubating the delivery vehicle construct with various cell types and determining the efficiency of uptake of the delivery vehicle construct into the cell.

In a particular aspect of the invention, it was demonstrated that human airway epithelia express uPAR by probing human airway epithelia cells with an anti-uPAR monoclonal antibody and detecting the presence of binding of the anti-uPAR monoclonal antibody by fluorescence-activated cell sorting. See FIG. 1B and Example 1 below. The presence of uPAR on the apical surface of human airway epithelia was demonstrated using immunocytochemistry of unpermeabilized epithelia (FIG. 1C and Example 1 below).

It was also demonstrated by a modified ELISA assay that full length uPA binds to the apical surface of differentiated human airway epithelia. See FIG. 2 and Example 2 below. In one embodiment of the invention, full length uPA binds to the apical surface of human airway epithelia at an affinity of between 0.1 nM to 1.0 mM. In a preferred embodiment of the invention, full length uPA binds to the apical surface of human airway epithelia at an affinity of between 20.0 nM to 1.0 μM. In addition, full length uPA stimulated increased fluid-phase endocytosis which was demonstrated by the uptake of Texas Red-conjugated dextran, a fluid phase marker in the presence of full length uPA. See FIG. 3B and Example 3 below. This stimulation of fluid-phase endocytosis was blocked by PI-PLC which cleaves GPI linkages and removes uPAR showing that uPAR is involved. (Note, uPAR is a GPI-linked receptor).

As with full length uPA, the u7 peptide of uPA (SEQ ID NO:1), which is key for binding to uPAR, also stimulated fluid phase endocytosis where as an equivalent peptide in which the amino acid sequence was scrambled (scrambled peptide; SEQ ID NO:2) did not. See FIG. 4 and Example 3 below. The ability of the u7 peptide to stimulate endocytosis demonstrates that the proteinase domain of uPA and the PAI-1 binding domain (previously shown to be required for endocytosis in uPAR expressing cells) are not required for the stimulation of fluid phase endocytosis.

Furthermore, full length uPA and the u7 peptide enhanced the uptake of a nonspecifically bound vector (both an adenoviral vector and an AAV vector). See FIG. 5A and Example 4 below. It has been shown that incorporating adenovirus or AAV in CaPi precipitates increases nonspecific binding to the apical surface and thereby enhances gene transfer. See Fasbender et al., *J. Clin. Invest.* 102:184–193 (1998); Lee et al., *Human Gene Ther.* 10:603–613 (1999); Walters et al., *J. Virol.* 74:535–540 (2000), all incorporated herein by reference. The administration of virus/CaPi coprecipitates does not increase the rate of apical endocytosis however. See Walters and Welsh, *Gene Ther.* 6:1845–1850 (1999) and U.S. patent application Ser. No. 09/082,510, both incorporated herein by reference. The treatment of airway epithelia with a virus:CaPi complex (serum free) in the presence of uPA and the u-7 peptide increased gene delivery 8–10 fold compared to the virus:CaPi complex alone. See FIG. 5A and Example 4 below. In addition, uPA was able to enhance gene delivery and could be detected even 2 weeks after the virus:CaPi complex was delivered to cells. See FIG. 5B and Example 4 below.

The disruption of tight junctions does not account for the increased uptake of the non specifically bound vector. Full length uPA and the u7 peptide also enhanced the uptake of a vector expressing CFTR in cystic fibrosis (CF) airway epithelia. See FIG. 5C and Example 4 below. The enhanced uptake of the CFTR expressing vector, increased the expression levels of CFTR in the airway epithelia. FIG. 5C also shows that a cAMP-stimulated current (i.e. corrected the Cl– channel defect in the CF airway epithelia) is created by the increased uptake of the CFTR-expressing vector. In addition, the u7 peptide also corrected the Cl– channel defect to a greater extent than the full length uPA.

The ability of uPA to stimulate endocytosis was also demonstrated with freshly excised monkey tracheal explants. FIG. 6A shows a control explant treated with FITC-dextran wherein there was a low level of basal endocytosis. See Example 5 below. The application of uPA stimulated the basal level endocytosis 3-fold over control levels. See FIGS. 6A through 6C and Example 5 below. In addition, uPA stimulated uptake of a vector into monkey tracheal explants 8-fold over basal levels. See FIGS. 6D, 6E and 6F and Example 5 below.

To demonstrate that uPA specifically linked to a vector could also enhance uptake of the vector into cells, u7-peptide-linked to polyethylene glycol (PEG) was coupled to the capsid of a recombinant adenoviral vector expressing β-galactosidase (βgal) to form a u7-PEG-βgal adenovirus complex. Uptake of the u7-PEG-βgal adenovirus complex was increased 10-fold as compared to the virus coupled to PEG alone or PEG linked to a mutated peptide (SEQ ID NO:3). See FIG. 7 and Example 6 below.

The present invention further provides physiological compositions including the delivery vehicle constructs comprising a uPA portion and a cargo portion of the present invention and further comprising a carrier. Where the physiological compositions are pharmaceutical compositions, they may be prepared by techniques known in the art and reference can be made to Remington's Pharmaceutical Sciences, 17th ed., Mack Publishing, Easton, Pa. The physiological forms of the present compositions suitable for administration into a subject include sterile aqueous solutions and dispersions. The physiological compositions of the present invention are compounded for administration in effective dosage amounts with a suitable acceptable carrier and/or diluent.

The precise effective amount of the compositions of the present invention can be determined by the ordinary skilled artisan with consideration of individual differences in age, weight, extent of disease and condition of the subject. It can generally be stated that the preparation of the present invention should be preferably administered in an amount of at least about one plaque forming unit per desired cell where the cargo is a virus.

It is also advantageous to formulate parenteral compositions in dosage unit form for ease of administration and uniformity of dosage. Dosage unit form as used herein refers to discrete units suited as unitary dosages for the subjects to be treated, each unit containing a predetermined quantity of active material calculated to produce the desired phenotypic effect in association with the required carrier. The specification of the novel dosage unit forms of the invention are dictated by and directly depend on the unique characteristics of the cargo and the limitations inherent in the art of compounding. In one aspect, the cargo of the present invention comprises a viral vector encoding CFTR, and an effective amount of the composition comprising the cargo is sufficient to correct the Cl⁻ channel defect in a CF subject.

The invention is further illustrated by the following examples which are not intended in any way to limit the scope of the invention.

EXAMPLES

Example 1

Human Airway Epithelia Express uPAR at the Apical Surface.

A. Cells, cultures. COS-1 cells were cultured in Dulbecco's Modified Eagle's media (DMEM, high glucose) supplemented with 10% fetal bovine serum (FBS; Sigma Chemical Co., St. Louis, Mich.), 100 U/ml penicillin and 100 µg/ml streptomycin (P/S).

Human airway epithelia were obtained from the tracheas and bronchi of lungs removed for organ donation. The University of Iowa In vitro Models Core isolated cells by enzyme digestion as described by Yamaya et al., *Am. J. Physiol.* 262:L713–724 (1992) and Zabner et al., *J. Virol.* 70:6994–7003 (1996), incorporated herein by reference. Freshly isolated cells were seeded at a density of 5×10$^5$ cells/cm$^2$ onto collagen coated, 0.6 cm$^2$ diameter Millicell polycarbonate filters (Millipore Corp., Bedford, Mass.). Cultures were maintained in a 37° C. incubator with 7% CO$_2$ and air. After 24 hours, media from the mucosal side was removed and cells were cultured at the air-liquid interface. Culture media consisted of a 1:1 mixture of DMEM and Ham's F12, 5% Ultraser G (Biosepra SA, Cedex, France), 100 U/ml penicillin, 100 µg/ml streptomycin, 1% nonessential amino acids, and 0.12 U/ml insulin.

B. Fluorescence-activated cell analysis: Human airway epithelia or COS-1 cells were washed once with PBS with 0.9 mM Ca$^{2+}$ and 0.9 mM Mg$^{2+}$. Cells were released from their substratum by a 10 min. incubation in 0.05% trypsin and 0.53 mM EDTA at 37° C. The cell suspension was collected and 1 ml of DMEM was added. Cells were centrifuged at 64 X g for 5 minutes. Cells were washed with PBS and centrifuged again. Cells were then treated with either PBS alone or with a murine, anti-human uPAR antibody (1:100, American Diagnostica, Greenwich, Conn.) at 4° C. for 2 hours. Following incubation, cells were centrifuged at 64 X g for 5 minutes. Cells were then washed with PBS and incubated with FITC-conjugated anti-mouse IgG (1:500, Jackson ImmunoResearch, West Grove, Pa.) for 1 hour at room temperature. Cells were centrifuged for 5 minutes at 64 X g, resuspended in PBS and analyzed by fluorescence-activated cells scans (FACS).

C. Immunocytochemistry: Human airway epithelia were chilled on ice for 15 minutes. All incubations were performed at 4° C. and followed by 3 washings of PBS. Cells were incubated with 0.05 M glycine for 25 minutes to quench free aldehydes, then washed with 5% BSA for one hour to block non-specific binding. Anti-human uPAR antibody (1:100, American Diagnostica) in PBS was added to the apical surface and incubated for 3 hours. FITC-conjugated anti-mouse IgG (1:500, Jackson ImmunoResearch) in PBS was added apically for 1 hour. Cells were fixed with 4% paraformaldehyde for 15 minutes, mounted on glass slides, and studied using confocal microscopy (MRC-1024, Biorad, Richmond, Calif.). Control cells were treated with FITC-conjugated anti-mouse IgG alone.

D. Analysis of uPAR Expression on the Apical Surface of Human Airway Epithelia: To address whether human airway epithelia express uPAR at the apical surface, primary cultures of epithelia were grown at the air-liquid interface under conditions that allow them to differentiate and develop morphological and functional properties of the native epithelium. See Yamaya et al., *Am J. Physiol.* 262:L713–724 (1992); Zabner et al., *J. Virol.* 70:6994–7003 (1996) (incorporated herein by reference). After at least two weeks in culture, cells were dissociated from the permeable support, probed with an anti-human uPAR monoclonal antibody and labeling was detected by fluorescence-activated cell sorting. FIG. 1A shows a control with COS-1 cells which are known to express uPAR. See Nykjaer et al, *J. Biol. Chem.* 269:25668–76 (1994) (incorporated herein by reference). FIG. 1B demonstrates that human airway epithelia also express uPAR. In addition, FIG. 1C, which is the immunocytochemistry of unpermeabilized epithelia, shows that uPAR (green fluorescence) is expressed on the apical surface of human airway epithelia. These data are indicative that uPAR may serve as a target for ligand applied to the luminal surface of human airway epithelia.

Example 2 uPA Binds uPAR in Airway Epithelia with High Affinity

A. uPA Sources: uPA was purchased from either Calbiochem-Nova Biochem Corp. (human urine, LaJolla, Calif.) or Sigma-Aldrich Inc. (human kidney cells, Milwaukee, Wis.). The u7-peptide (CLNGGTC; SEQ ID NO:1), a scrambled peptide (CTCGNCL; SEQ ID NO:2) and a mutated peptide (CLNFFTC; SEQ ID NO:3) were synthesized by the University of Iowa Peptide Synthesis Core.

B. ELISA on Human Airway Epithelia: Human airway epithelia were chilled on ice for 15 minutes. Following 3 washes in PBS, non-specific binding was blocked with 1× TBS (137 mM NaCl, 2.7 mM KCl, 2.5 mM Tris) and 5% milk for 1 hour on ice. All incubations were followed by 3 washes with PBS unless otherwise indicated. Varying concentrations of uPA were applied apically for 30 minutes on ice. Cells were then fixed with 4% paraformaldehyde for 15 minutes. Bound uPA was detected by apical incubation with a mouse monoclonal anti-human uPA antibody (1:1000 in 1× TBS+5% milk, American Diagnostica) for 1 hour at 37° C. Anti-mouse IgG-HRP (1:5000 in 1× TBS+5% milk, Amersham Pharmacia Biotech, Inc., Piscataway, N.J.) was then applied apically for 1 hour at 37° C. TMBD substrate buffer (3,3', 5,5', tetramethyl benzidine dihydrochloride in 0.1 M citric acid, 0.2 M Na$_2$HPO$_4$, pH 5.0) was added apically for 5 minutes at room temperature in the dark. TMBD substrate buffer was removed and the reaction was stopped with 2N H$_2$SO$_4$. Color change of substrate was read at 450 nm (OD$_{450}$) in a plate reader.

C. Binding of uPA to uPAR in Human Airway Epithelia: Binding of uPA to differentiated human airway epithelia was tested using the modified ELISA described above. FIG. 2 shows that uPA bound to the apical surface and that half maximal binding occurred at approximately 50 nM. Comparatively, studies in HeLa cells reported an EC50 for binding of uPA to uPAR of approximately 400 nM. See Estreicher et al., *J. Biol. Chem.* 264:1180–9 (1989). The data suggest that a high affinity interaction between uPA and uPAR is preserved in human airway epithelia.

Example 3

Apical uPA increased Fluid-Phase Endocytosis

A. Explants: Freshly excised monkey tracheas were maintained on ice. Explants (1 cm$^2$) were maintained in 1:1

DMEM and Ham's F12 supplemented with 2% Ultraser G (Biosepra SA) in a 37° C. incubator.

B. Assay for Fluid Phase Endocytosis: Cells were chilled on ice for 15 minutes and then incubated with 50 nM uPA or 0.15 μM u7-peptide (SEQ ID NO:1) added to the apical surface for 30 minutes at 4° C. Following 3 washes in PBS, cells were incubated with 0.5 mg/ml Texas Red-labeled fixable dextran (3,000 MW, Molecular Probes, Eugene, Oreg.) for 10 minutes at 37° C. Following 3 washes in PBS, cells were fixed with 4% paraformaldehyde, mounted onto class slides with Vectashield (Vector Laboratories, Inc., Burlingame, Calif.), and viewed by fluorescence microscopy. Control cells were incubated with Texas Red-labeled dextran alone to measure basal levels of endocytosis. Monkey tracheal explants were assayed as described for primary cell cultures. To evaluate time-dependent changes, cells were treated as described above with uPA (50 nM) followed by incubations in Texas Red dextran for 5, 10, 30 or 60 minutes at 37° C. To evaluate the requirement of GPI-anchored receptor for uPA stimulated endocytosis, human airway epithelia were incubated with phosphatidylinositol-specific phospholipase C prior to incubations with uPA and Texas Red dextran, (PI-PLC from *Bacillus cereus*, Molecular Probes) for 2 hours at 37° C. followed by 3 washes in PBS to cleave uPAR (see Hoppe-Seyler, *Biol. Chem.* 376:143–155 (1995).

B. Effect of uPA on Fluid Phase Endocytosis in Human Airway Epithelia: Stimulation of endocytosis by uPA was determined by measuring the uptake of Texas Red-conjugated dextran, a fluid phase marker. FIG. 3A shows that under basal conditions, few human airway epithelia cells took up dextran from the apical solution. This result is consistent with earlier work suggesting a low level of apical endocytosis in airway epithelia. See Pickles et al., *J. Virol.* 72:6014–23 (1998) and Fasbender et al., *Gene Ther.* 4:1173–80 (1997) (incorporated herein by reference). Surprisingly, following apical addition of uPA (50 nM), there was a marked increase in the number of cells that took up the fluid phase marker (see FIG. 3B). The data suggest that binding of uPA to uPAR in human airway epithelia stimulates endocytosis.

C. Determination of Time of Internalization Following uPA Binding: To determine how quickly internalization follows ligand binding, human airway epithelia were incubated with apical uPA (50 nM) at 4° C. for 30 minutes. Cells were then incubated with labeled-dextran for 5 to 60 minutes at 37° C. An increase in stimulated uptake was apparent by 5 minutes and the uptake continued to increase for at least 30 minutes (see FIG. 3E). By 60 minutes, the dextran fluorescence developed a more vesicular appearance, suggesting intracellular accumulation in late stage endosomes or lysosomes. Removal of uPAR by incubation with PI-PLC, which cleaves GPI linkages, eliminated the endocytosis response (see FIG. 3F). Taken together, the data indicate that uPA potently stimulates endocytosis in human airway epithelia and that the stimulation is likely mediated through uPAR.

D. Effect of u7-peptide on Fluid Phase Endocytosis in Human Airway Epithelia: Studies by Appella et al,*J. Biol. Chem.* 262:4437–40 (1987) (incorporated herein by reference) identified a N-terminal portion of uPA that is key for binding to uPAR comprising residues 13–19 (CLNGGTC; SEQ ID NO:1). The U7-peptide was synthesized and examined for its ability to stimulate endocytosis. As with full length uPA, application of the u7-peptide (SEQ ID NO:1) to the apical surface of human airway epithelia stimulated fluid phase endocytosis, whereas an equivalent peptide in which the sequence was scrambled (scrambled peptide; SEQ ID NO:2) did not (see FIG. 4). The data show that binding of a small peptide from uPA which does not comprise the C-terminus of uPA, nor the proteinase domain of uPA containing the PAI-1 binding region of uPA, stimulated endocytosis. Since the u7-peptide does not contain the proteinase domain containing the sequences previously shown to be required for uPA to bind PAI-1, these data also show that uPA:PAI-1 complex surprisingly is not required to stimulate endocytosis in human airway epithelia.

Example 4 uPA Enhances Gene Transfer by Non-specifically Bound Vector to Human Airway Epithelia A. Recombinant Adenovirus and AAV: Recombinant adenovirus vectors expressing β-galactosidase (Ad2/β-Gall-4; U.S. Pat. No. 5,882,877, incorporated herein by reference) and CFTR (Ad2/CFTR-16; PCT Publication WO/9846781, incorporated herein by reference) were prepared as described previously by Lee et al., *Human Gene Ther.* 10:603–13(1999) (incorporated herein by reference) by the University of Iowa Gene Transfer core at titers of approximately $10^{10}$ infectious units/ml. Recombinant AAV2 vector expressing β-galactosidase was provided by Cf. Jay Chiorini (NIH) at approximately $1 \times 10^7$ IU/ml (Chiorini et al., *J. Virol.* 73:1309–1319 (1999)).

B. Evaluation of Gene Transfer: The apical surface of human airway epithelia was washed once with PBS. Adenovirus was applied at a multiplicity of infection (MOI) of 50 to the apical surface for 30 minutes at 37° C. Adenovirus was applied either alone or in a CaPi coprecipitate as previously described by Fasbender et al., *J. Clin. Invest.* 102:184–193 (1998) and Lee et al., *Hum. Gene Ther.* 10:603–13 (1999) (incorporated herein by reference). Following 3 washes, cells were returned to the incubator and assayed for gene transfer 48 hours later. AAV2 was applied at an MOI<1 to the apical surface for 30 minutes at 37° C. AAV2 was applied either alone or on a CaPi coprecipitate formed as previously described by Fasbender et al. and Lee et al. for adenovirus. Following 3 washes, cells were returned to the incubator and assayed for gene transfer 14 days later. Total β-galactosidase activity was measured using a commercially available technique (Galacto-Light, Topix, Bedford, Mass.).

Monkey tracheal explants were infected as described for primary cells. Following infection, explants were maintained in a 37° C. incubator for 72 hours and then stained with X-gal. For X-gal staining, explants were fixed with 1.8% formaldehyde and 2% glutaraldehyde, and then incubated at 37° C. in X-gal solution overnight.

C. Measurement of Transepithelial Electrical Properties: Epithelia were mounted in modified Ussing chambers (Jim's Instruments, Iowa City, Iowa) and bathed with Ringer's solution on their submucosal side (135 mM NaCl, 2.4 $K_2HPO_4$, 0.6 mM $KH_2PO_2$, 1.2 mM $CaCl_2$, 1.2 mM $MgCl_2$, 5 mM Hepes, pH 7.4 and 10 mM dextrose). The mucosal surface was bathed in the identical solution, except that 135 mM NaGluconate replaced the 135 mM NaCl. In this way, a transepithelial Cl$^-$ concentration gradient was established in order to magnify changes in Cl− transport. The transepithelial Na$^+$ transport was blocked with mucosal amiloride (10 μM). Mucosal DIDS (100 μM) blocked non-CFTR Cl⁻ transport. The cAMP agonists, forskolin (10 μM) and IBMX (100 μM) were applied to both solutions to stimulate transepithelial Cl⁻ transport via CFTR.

D. uPA Enhancement of Gene Transfer: The ability of uPA to enhance gene transfer by nonspecifically bound vector was tested. Incorporation of adenovirus or AAV in CaPi coprecipitates increases non-specific virus binding to the apical surface and thereby enhances gene transfer. However, administration of CaPi coprecipitates, alone, does not increase the rate of apical endocytosis and depends upon the basal rate of endocytosis. In contrast, the addition of uPA (50 nM) to the apical surface of human airway epithelia and the subsequent administration of CaPi:adenovirus coprecipitates increased gene transfer 8–10 fold as compared to the coprecipitate alone when assayed for gene transfer forty-eight hours after the administration of the coprecipitates (see FIG. 5A). Similar results were also obtained with CaPi:AAV coprecipitates; FIG. 5B shows that uPA enhanced gene transfer when measured 2 weeks after AAV was delivered in a CaPi coprecipitate. No effect was seen on the integrity of tight junctions which has previously been shown to allow access of viral vectors to the basolateral surface where they bind receptors. The u7-peptide (SEQ ID NO:1), which has no enzymatic activity, had an effect similar to uPA, and stimulated fluid phase endocytosis across the apical membrane. Finally, disrupting tight junctions by chelating Ca²⁺ did not enhance gene transfer by Ad/βgal:CaPi. Tight junction integrity was measured by transepithelial resistance which did not change following uPA or u7 treatment. These data indicate that disruption of tight junctions did not account for the enhanced gene transfer.

The ability of uPA to enhance gene transfer and expression of CFTR in differentiated CF airway epithelia was also tested. FIG. 5C shows that gene transfer with an adenovirus expressing CFTR in a CaPi coprecipitate generated a cAMP-stimulated current. The u7-peptide further enhanced the correction. The data show that the u7-peptide targets cells involved in generating transepithelial Cl⁻ transport.

Example 5

The Ability of uPA to Stimulate Endocytosis and Gene Transfer in Monkey Tracheal Explants As an additional test of uPA-mediated endocytosis and gene transfer, freshly excised monkey tracheal explants were tested. FIG. 6A shows a control explant treated with FITC-dextran only, as with human epithelia, there was a low level of basal endocytosis. In contrast, apical application of uPA stimulated endocytosis 3-fold over control levels (see FIGS. 6A through 6C). The effect of uPA on Ad:CaPi-mediated gene transfer was also assayed. Control explants infected apically with Adenovirus:CaPi coprecipitates alone had low levels of gene transfer (see FIG. 6D). However, if uPA was first applied to the apical surface and followed by the application of the Adenovirus:CaPi coprecipitate, there was an approximately 8-fold increase in gene transfer (see FIGS. 6E and 6F). This section of X-gal-stained explants showed both ciliated and non-ciliated cells expressed the β-galactosidase gene (see FIG. 6G).

Example 6 uPA Enhances Gene Transfer by Specifically Bound Vector to Human Airway Epithelia A. Covalent Attachment of u7-peptide to Adenovirus: Bifunctional PEG molecules were added to virus at room temperature for 60 minutes to allow coupling of PEG to viral surface proteins. See O'Riordan et al., *Human Gene Ther.* 10:1349–1358 (1999) (incorporated herein by reference). Unreacted PEG was separated from the PEGylated virus by CsCl centrifugation as described previously and PEGylated virus (Ad2/PEG) was finally dialyzed into phosphate-buffered saline (pH 7.0) containing 5% sucrose. u7-peptide and mutated peptides synthesized to include a terminal cysteine with a free sulfhydryl were dissolved in PBS containing 5% sucrose to a final concentration of 10 mM and added to $1.5 \times 10^{12}$ particles of Ad2/PEG at a final concentration of 1 mM. The peptide and PEG virus were allowed to couple for 4 hours at room temperature. Unreacted peptide was removed from Ad2/PEG/peptide by dialysis into PBS containing 5% sucrose.

Figure 7:
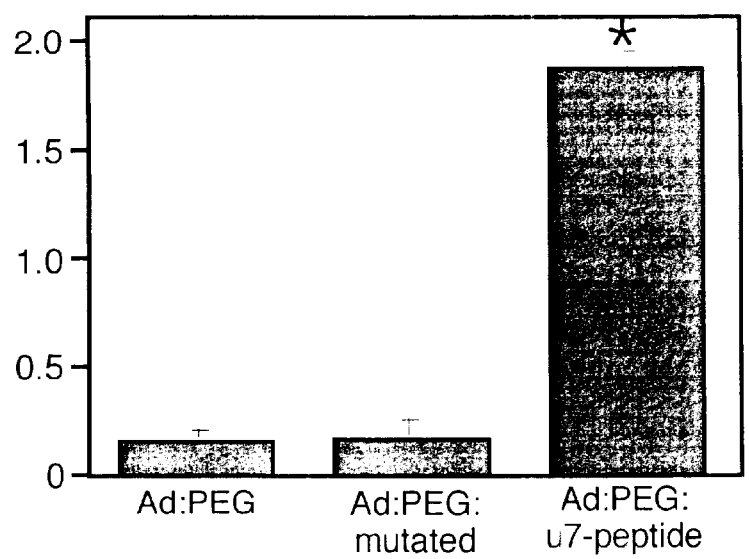
FIG. 7: Targeting an adenovirus vector (Ad2/βgal-4) to uPAR by covalent association of u7-peptide (SEQ ID NO:1) and PEG to the adenovirus capsid. "PEG:mutated" refers to a mutated u7-peptide sequence (SEQ ID NO:3) (n=6). Asterisk indicated $p \leq 0.05$.

B. Specific Coupling of uPA to Vector Enhances Gene Transfer: The u7-peptide (SEQ ID NO:1) was coupled to the capsid of an adenovirus expressing β-galactosidase using PEG as described above. As controls, PEG alone and PEG linked to a mutated peptide (SEQ ID NO:3) were also coupled to adenovirus. FIG. 7 shows that coupling of the u7-peptide to the vector via PEG enhanced gene transfer to airway epithelia 10-fold.

We claim:

1. A delivery vehicle construct comprising a cargo portion and a urokinase plasminogen activator (uPA) portion consisting essentially of a u7-peptide (SEQ ID NO:1), wherein the uPA portion facilitates delivery of the cargo portion into a target cell.

2. The delivery vehicle construct of claim 1 wherein the cargo portion is linked to the u7-peptide portion.

3. The delivery vehicle construct of claim 1 wherein the cargo is selected from the group consisting of viral and non-viral vectors.

4. The delivery vehicle construct of claim 3 wherein the cargo is selected from the group consisting of adenovirus and adeno-associated virus (AAV).

5. A method for delivering a delivery vehicle construct which comprises a cargo portion and a uPA portion consisting essentially of a u7-peptide (SEQ ID NO:1) to a cell said method comprising contacting said cell with said delivery vehicle construct under conditions wherein the construct is delivered to the cell, and wherein the uPA portion facilitates delivery of the cargo portion to the cell.

6. A method of delivering a delivery vehicle construct which comprises a cargo portion and a uPA portion to airway epithelia said method comprising contacting said airway epithelia with said delivery vehicle construct for a time and under conditions sufficient to allow delivery of the vehicle construct to the airway epithelia, wherein the uPA portion facilitates delivery of the cargo portion to the cell.

7. The method of claim 6 wherein the uPA portion of the construct is selected from the group consisting of the u7-peptide (SEQ ID NO:1), full length uPA and uPA deficient for PAI-1 binding.

8. The method of claim 6 wherein the cargo portion of the construct is selected from the group consisting of viral and non-viral vectors.

9. The method of claim 8 wherein the cargo portion is selected from the group consisting of adenovirus and AAV.

10. The method of claim 6 wherein the cargo portion comprises a nucleic acid encoding cystic fibrosis transmembrane conductance regulator (CFTR).

* * * * *

UNITED STATES PATENT AND TRADEMARK OFFICE
CERTIFICATE OF CORRECTION

PATENT NO. : 6,649,597 B1
DATED : November 18, 2003
INVENTOR(S) : Welsh et al.

It is certified that error appears in the above-identified patent and that said Letters Patent is hereby corrected as shown below:

Title page,
Item [56], References Cited, U.S. PATENT DOCUMENTS, insert -- 6,086,870 A 7/2000 --;
OTHER PUBLICATIONS, insert:
Drapkin et al. (first occurrence), "Clnical" should read -- Clinical --;
Quax et al., "Urokinae-Type" should read -- Urokinase-Type --;
Czekay et al., "Comlexes" should read -- Complexes --;
Kollen et al., "APolylysines" should read -- Polylysines --;
Lu et al., "Endothelila" should read -- Endothelial --;
Dumler et al., "plasminogenactivator" should read -- plasminogen activator --;
Kobayashi et al., "Metastsis" should read -- Metastasis --;
Moestrup et al., "Plaminogen" should read -- Plasminogen --;
Yamaya et al., "Stuctur" should read -- Stucture --; and "Trachela" should read -- Tracheal --;
Boyd et al., "Urokinae" should read -- Urokinase --;
Miggnatti et al., "Miggnatti" should read -- Mignatti --; and "Invation" should read -- Invasion --;
Stoppelli et al., "uokinase" should read -- urokinase --; and Vassalli et al., "SIte" should read -- Site --

Column 1,
Line 4, insert -- This invention was made with government support under Government NHLBI Grant Number HL 51670. Therefore, the United States Government has certain rights in the invention. --

INTRODUCTION

The present invention relates to the targeted delivery of a delivery vehicle construct which specifically binds to and stimulates endocytosis into cells expressing the urokinase plasminogen activator receptor (uPAR), and particularly human airway epithelia. The delivery vehicle construct comprises an internalizing portion and a "cargo" portion which are linked together and is useful for the targeted delivery of the "cargo" to cells expressing uPAR and particularly human airway epithelia. --

UNITED STATES PATENT AND TRADEMARK OFFICE
CERTIFICATE OF CORRECTION

PATENT NO.    : 6,649,597 B1
DATED         : November 18, 2003
INVENTOR(S)   : Welsh et al.

It is certified that error appears in the above-identified patent and that said Letters Patent is hereby corrected as shown below:

Column 2,
Line 30, "extracelluar" should read -- extracellular --
Lines 59-60, "phenomenon" should read -- phenomena --

Column 3,
Line 9 "Clatherin-dependent" should read -- Clathrin-dependent --

Column 6,
Line 8, "13-19described" should read -- 13-19 described --
Lines 47 and 53, "u7-peptide" should read -- u7 peptide --
Line 64, "Cl–" should read -- Cl⁻ --

Column 7,
Line 2, "FIGS. 1*a-c*" should read -- FIGS. 1A-C --
Line 19, "(D)" should be deleted
Line 23, "u7-peptide" (both occurrences) should read -- u7 peptide --
Line 27, "u7-peptide" should read -- u7 peptide --
Line 32, "FIGS. 5*a-c*" should read -- FIGS. 5A-C --
Line 33, "(a)" should read -- (A) --
Line 41, "FIGS. 6*a-g*" should read -- FIGS. 6A-G --
Line 52, "u7-peptide" should read -- u7 peptide --
Line 54, "u7-peptide" should read -- u7 peptide --

Column 8,
Line 7, "cystine" should read -- cysteine --
Line 47, "Illarvirus" should read -- Ilarvirus --
Line 50, "icroviridae" should read -- Icroviridae --
Line 56, "Prodoviridae" should read -- Podoviridae --

Column 10,
Lines 21-22, "polyalkalene" (both occurrences) should read -- polyalkylene --

UNITED STATES PATENT AND TRADEMARK OFFICE
CERTIFICATE OF CORRECTION

PATENT NO.    : 6,649,597 B1
DATED         : November 18, 2003
INVENTOR(S)   : Welsh et al.

It is certified that error appears in the above-identified patent and that said Letters Patent is hereby corrected as shown below:

Column 11,
Line 25, "where as" should read -- whereas --
Line 47, "u-7 peptide" should read -- u7 peptide --
Line 54, "non specifically" should read -- nonspecifically --
Lines 60 and 65, "Cl–" should read -- Cl⁻ --

Column 12,
Line 13, "u7-peptide-linked" should read -- u7 peptide linked --

Column 14,
Line 26, "u7-peptide" should read -- u7 peptide --

Column 15,
Line 5, "u7-peptide" should read -- u7 peptide --
Line 11, "class" should read -- glass --
Line 28, "B." should read -- C. --
Line 43, "C." should read -- D. --
Line 47, "labeled-dextran" should read -- labeled dextran --
Line 59, "D." should read -- E. --; and "u7-peptide" should read -- u7 peptide --
Line 64, "U7-peptide" should read -- u7 peptide --
Line 67, "u7-peptide" should read -- u7 peptide --

Column 16,
Line 8, "u7-peptide" should read -- u7 peptide --
Line 66, "Cl–" should read -- Cl⁻ --

Column 17,
Lines 25, 39 and 40, "u7-peptide" should read -- u7 peptide --.

Column 18,
Lines 23, 32, 42 and 47, "u7-peptide" should read -- u7 peptide --

UNITED STATES PATENT AND TRADEMARK OFFICE
CERTIFICATE OF CORRECTION

PATENT NO.    : 6,649,597 B1
DATED         : November 18, 2003
INVENTOR(S)   : Welsh et al.

It is certified that error appears in the above-identified patent and that said Letters Patent is hereby corrected as shown below:

Column 19,
Lines 27 and 31, "u7-peptide" should read -- u7 peptide --
Line 38, "delivering" should read -- facilitating the delivery of --
Line 40, "u7-peptide" should read -- u7 peptide --; and "cell said" should read -- cell, said --

Column 20,
Line 24, "delivering" should read -- facilitating the delivery of --
Line 26, "epithelia said" should read -- epithelia, said --
Line 33, "u7-peptide" should read -- u7 peptide --

Signed and Sealed this

Sixth Day of April, 2004

JON W. DUDAS
*Acting Director of the United States Patent and Trademark Office*

SEQUENCE LISTING

<160> NUMBER OF SEQ ID NOS: 3

<210> SEQ ID NO 1
<211> LENGTH: 7
<212> TYPE: PRT
<213> ORGANISM: Homo sapiens

<400> SEQUENCE: 1

Cys Leu Asn Gly Gly Thr Cys
1               5

<210> SEQ ID NO 2

-continued

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

Cys Thr Cys Gly Asn Cys Leu
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Cys Leu Asn Phe Phe Thr Cys
1               5
```